(12) United States Patent
Yazawa et al.

(10) Patent No.: US 7,985,384 B2
(45) Date of Patent: Jul. 26, 2011

(54) ANALYSIS KIT FOR LIVING ORGANISM AND CHEMICAL REACTION

(75) Inventors: Yoshiaki Yazawa, Nishitokyo (JP); Takashi Anazawa, Koganei (JP); Kenko Uchida, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 42 days.

(21) Appl. No.: 11/812,156

(22) Filed: Jun. 15, 2007

(65) Prior Publication Data

US 2007/0292897 A1    Dec. 20, 2007

(30) Foreign Application Priority Data

Jun. 19, 2006    (JP) ................... 2006-169146

(51) Int. Cl.
*G01N 21/75* (2006.01)
*G01N 31/22* (2006.01)
*G01N 33/52* (2006.01)

(52) U.S. Cl. .......... 422/420; 422/50; 422/400; 422/401; 422/402; 436/518; 436/164; 436/169; 436/172; 435/7.1; 435/283.1; 435/287.1; 435/287.2; 435/288.7

(58) Field of Classification Search .............. 422/50, 422/400, 401, 402, 420; 436/518, 164, 169, 436/172; 435/7.1, 283.1, 287.1, 287.2, 287.7, 435/288.7
See application file for complete search history.

(56) References Cited

U.S. PATENT DOCUMENTS

| | | | | |
|---|---|---|---|---|
| 5,424,193 A | * | 6/1995 | Pronovost et al. | 435/7.32 |
| 6,087,114 A | * | 7/2000 | Rider | 435/7.2 |
| 6,217,744 B1 | * | 4/2001 | Crosby | 205/775 |
| 6,235,241 B1 | | 5/2001 | Catt et al. | |
| 7,157,050 B2 | | 1/2007 | Yazawa et al. | |
| 2005/0221504 A1 | * | 10/2005 | Petruno et al. | 436/524 |
| 2006/0055930 A1 | | 3/2006 | Yamauchi | |

(Continued)

FOREIGN PATENT DOCUMENTS

JP    10-274624    11/1994

(Continued)

OTHER PUBLICATIONS

Kawakami, C., et al., "Influenza", vol. 6, No. 4, 2005, pp. 309-316 (In Japanese with English summary).

(Continued)

*Primary Examiner* — Melanie J Yu
(74) *Attorney, Agent, or Firm* — Stites & Harbison PLLC; Juan Carlos A. Marquez, Esq.

(57) ABSTRACT

There is provided a simple, inexpensive reaction analysis kit and system capable of performing highly sensitive, quantitative measurement. A chemical luminescence reaction is employed and a sensor element is used to detect the reaction in a highly sensitive manner. That is, a reaction detection plate is used to transmit a signal detected in the sensor element via a reader coil and a reader and then analyze the reaction. The reaction detection plate has a) a membrane, b) a first antibody impregnated section that is disposed such that it faces the membrane and holds a first labeled antibody that specifically binds to a substance to be analyzed, c) a second antibody immobilized section that is provided in part of the membrane and has an immobilized second antibody, the second antibody specifically binding to the substance to be analyzed, and d) a sensor element that is disposed such that it faces the second antibody immobilized section and includes a light detector and a signal transceiver.

4 Claims, 21 Drawing Sheets

U.S. PATENT DOCUMENTS

| | | | |
|---|---|---|---|
| 2006/0202665 A1* | 9/2006 | Hsu | 320/139 |
| 2007/0189928 A1* | 8/2007 | Sabol | 422/82.03 |
| 2008/0190172 A1* | 8/2008 | Jones | 73/23.2 |

FOREIGN PATENT DOCUMENTS

| | | |
|---|---|---|
| JP | 2004-101253 | 9/2002 |
| JP | 2004-170217 | 11/2002 |
| JP | 2005-077264 | 9/2003 |

OTHER PUBLICATIONS

Nikkei Medical, Nov. 2003, pp. 45-49 (In Japanese with English summary).

Nikkei Medical, Feb. 2003, pp. 54-55, (In Japanese with English summary).

Ohman, E. Magnus, et al., "The New England Journal of Medicine", vol. 335, No. 18, Oct. 1996, pp. 1333-1341.

Christenson, Robert H., et al., "Cardiac troponin T and cardiac troponin I: relative values in short-term risk stratification of patients with acute coronary syndromes", Clinical Chemistry 44, No. 3, 1998, pp. 494-501.

Stubbs, MD, Peter, et al., "Prognostic Significance of Admission Troponin T Concentrations in Patients with Myocardial Infarction", circulation, vol. 94, No. 6, Sep. 15, 1996, pp. 1291-1297.

Finkenzeller, Klaus, "RFID Handbook Radio-Frequency Identification Fundamentals and Applications", John Wiley & Son, Ltd., 1999, pp. 1-3 with Summary page.

* cited by examiner

Fig. 1
(a)
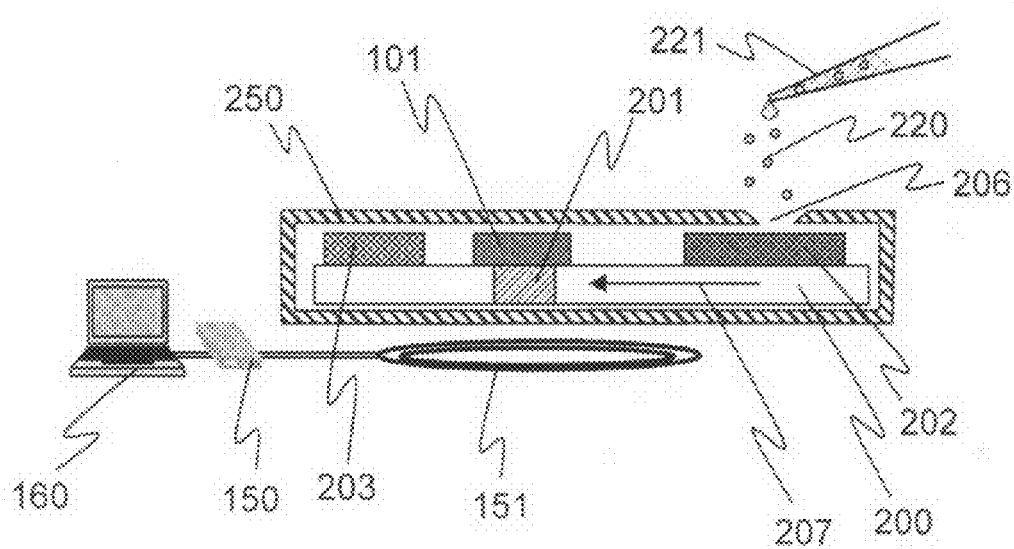
(b)
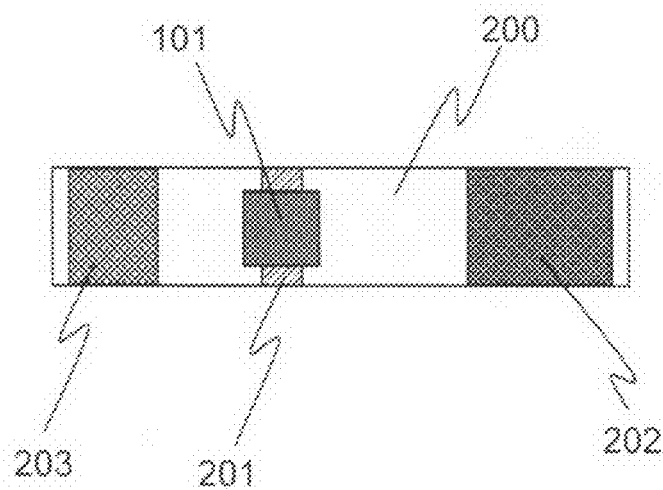

| ○ | ANTIGEN | 220 |
| Y | IMMOBILIZED ANTIBODY | 222 |
| Ⓔ | ENZYME | 223 |
| Y-Ⓔ | MODIFIED ANTIBODY | 224 |
| ★ | LUMINESCENCE SUBSTRATE | 225 |

Fig. 4
(a)
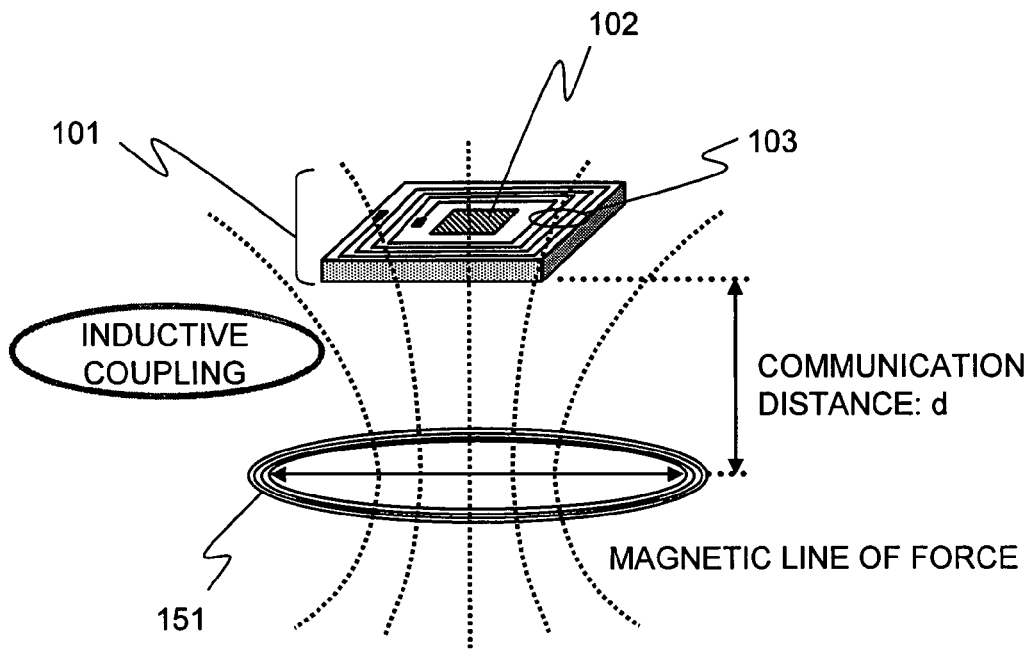
(b)
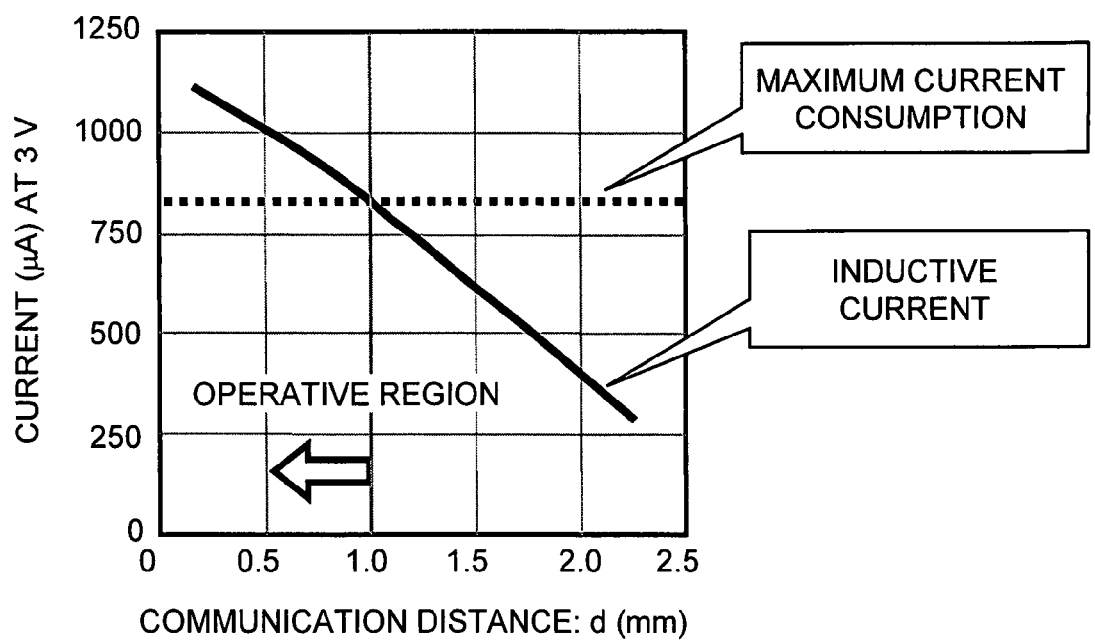

Fig. 5

(a) SOLID ANGLE CALCULATION MODEL

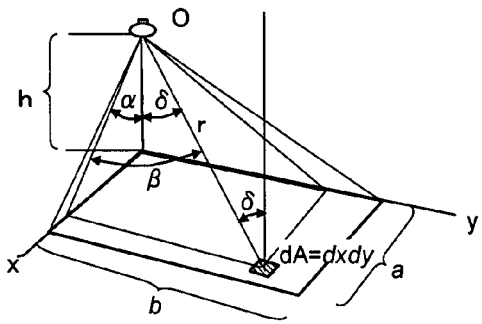

(b)

Determine solid angle $\Omega_{ab}$ formed when rectangle having side a and side b subtends origin o situated at a height of h above one apex of rectangle. Letting $\Omega_0$ be unit solid angle, 1 sr (steradian) and considering that effective size of area element dA in direction $\delta$ toward origin o is $dA\cos\delta$, since $d\Omega = (dA/r^2)\cos\delta\, \Omega_0$., $\cos\delta = \cos\alpha \cos\beta$ and $dA = dx\, dy$, double integrate them along with $\cos^2\alpha = h^2/(h^2+x^2)$ and $\cos^2\beta = (h^2+x^2)/(h^2+x^2+y^2)$ to obtain $\Omega$.

$$\Omega_{ab} = \int_{x=0}^{a}\int_{y=0}^{b} \frac{d\left(\frac{a}{h}\right) d\left(\frac{y}{h}\right)}{\left[1+\left(\frac{x}{h}\right)^2 + \left(\frac{y}{h}\right)^2\right]^{3/2}} \Omega_0 \qquad \Omega_{ab} = \sin^{-1}\left\{\frac{\frac{a}{h}}{\sqrt{1+\left(\frac{a}{h}\right)^2}} \cdot \frac{\frac{b}{h}}{\sqrt{1+\left(\frac{b}{h}\right)^2}}\right\} \Omega_0$$

(c)

INSTALLABLE SENSOR

| a | 1.0 mm |
| b | 1.0 mm |

| h | $\Omega$ab (sr) | 4x$\Omega$ab (sr) | 4x$\Omega$ab/4$\pi$ | LOSS DUE TO TRANSPARENT WINDOW 0.9·0.9 |
|---|---|---|---|---|
| 0.01 | 1.56 | 6.23 | 0.495 | 0.401 |
| 0.10 | 1.43 | 5.72 | 0.455 | 0.369 |
| 0.20 | 1.29 | 5.17 | 0.411 | 0.333 |
| 0.50 | 0.93 | 3.71 | 0.295 | 0.239 |
| 1.00 | 0.52 | 2.09 | 0.167 | 0.135 |
| 1.50 | 0.31 | 1.25 | 0.100 | 0.081 |
| 2.00 | 0.20 | 0.81 | 0.064 | 0.052 |
| 2.50 | 0.14 | 0.55 | 0.044 | 0.036 |
| 3.00 | 0.10 | 0.40 | 0.032 | 0.026 |
| 3.50 | 0.08 | 0.30 | 0.024 | 0.019 |
| 4.00 | 0.06 | 0.24 | 0.019 | 0.015 |
| 4.50 | 0.05 | 0.19 | 0.015 | 0.012 |
| 5.00 | 0.04 | 0.15 | 0.012 | 0.010 |
| 5.50 | 0.03 | 0.13 | 0.010 | 0.008 |
| 6.00 | 0.03 | 0.11 | 0.009 | 0.007 |

SENSOR CHIP WITH COMMUNICATION CAPABILITY

| a | 0.16 mm |
| b | 0.31 mm |

| h | $\Omega$ab (sr) | 4x$\Omega$ab (sr) | 4x$\Omega$ab/4$\pi$ |
|---|---|---|---|
| 0.01 | 1.501 | 6.00 | 0.478 |
| 0.10 | 0.939 | 3.76 | 0.299 |
| 0.20 | 0.553 | 2.21 | 0.176 |
| 0.50 | 0.161 | 0.65 | 0.051 |
| 1.00 | 0.047 | 0.19 | 0.015 |
| 1.50 | 0.021 | 0.09 | 0.007 |
| 2.00 | 0.012 | 0.05 | 0.004 |
| 2.50 | 0.008 | 0.03 | 0.003 |
| 3.00 | 0.005 | 0.02 | 0.002 |
| 3.50 | 0.004 | 0.02 | 0.001 |
| 4.00 | 0.003 | 0.01 | 0.001 |
| 4.50 | 0.002 | 0.01 | 0.001 |
| 5.00 | 0.002 | 0.01 | 0.001 |
| 5.50 | 0.002 | 0.01 | 0.001 |
| 6.00 | 0.001 | 0.01 | 0.000 |

Fig. 7
(a)
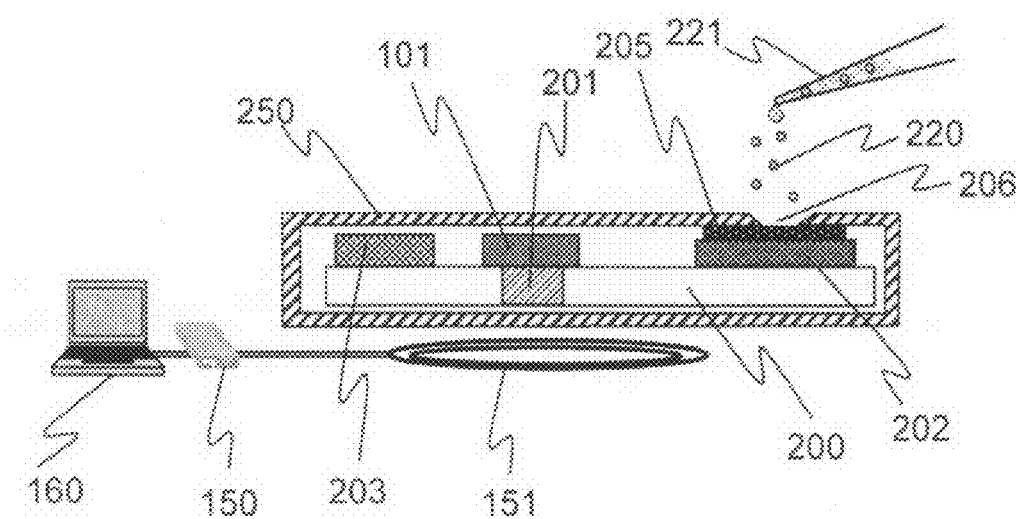
(b)
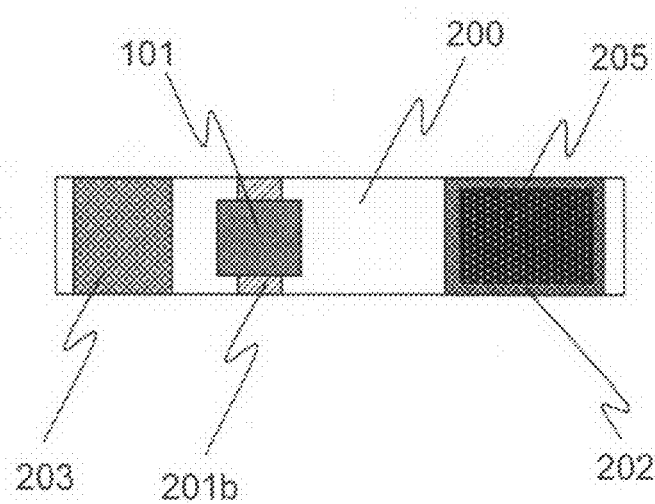

Fig. 8
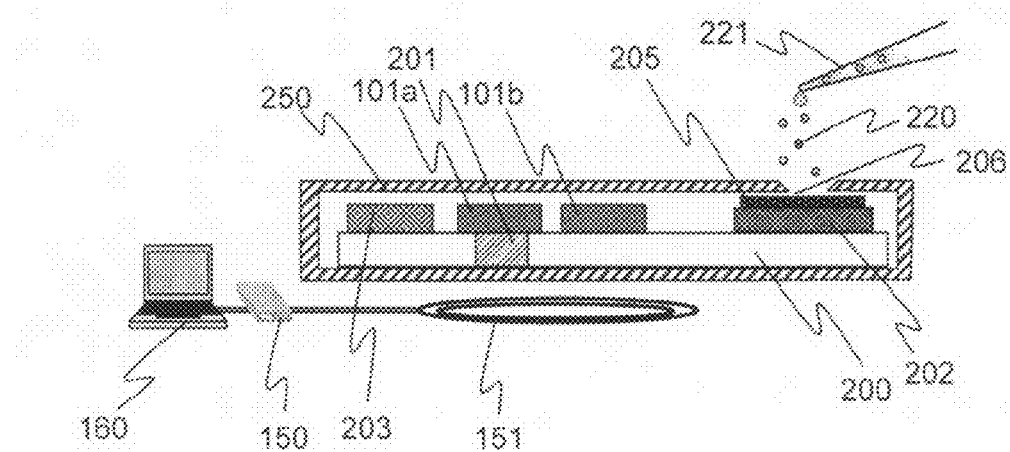
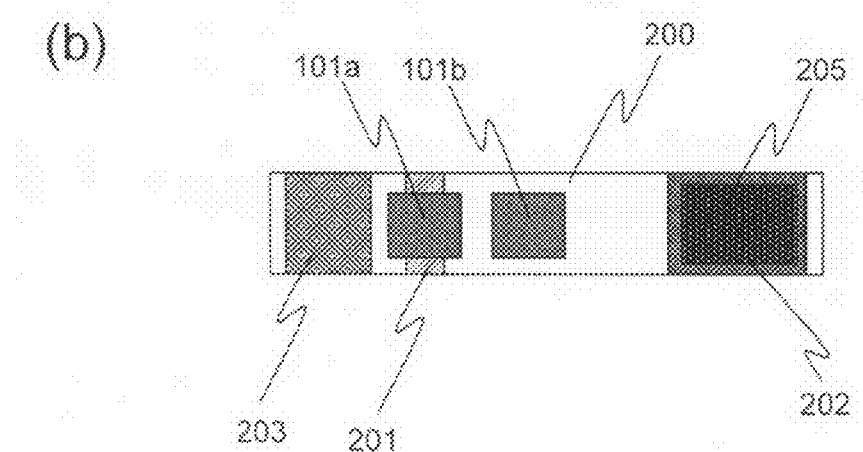
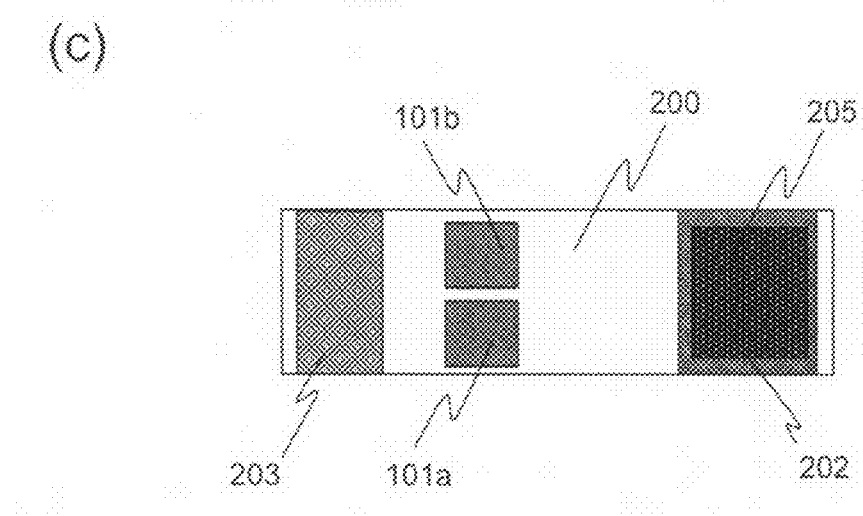

Fig. 11
(a)
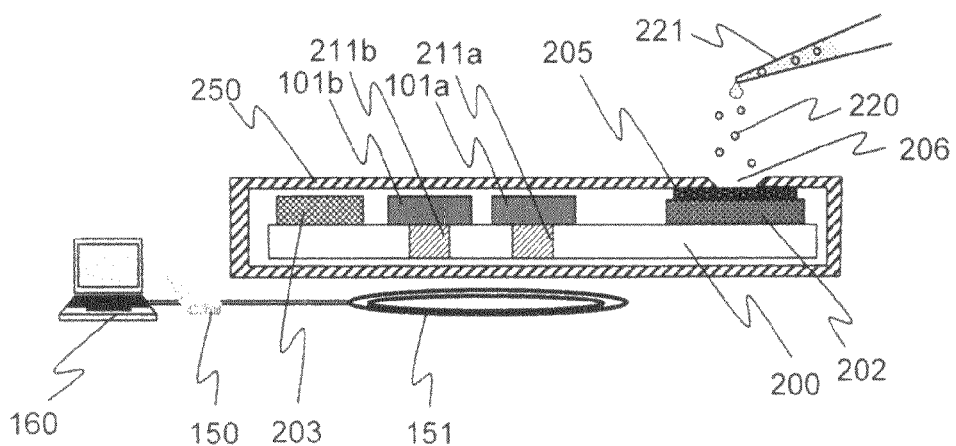
(b)
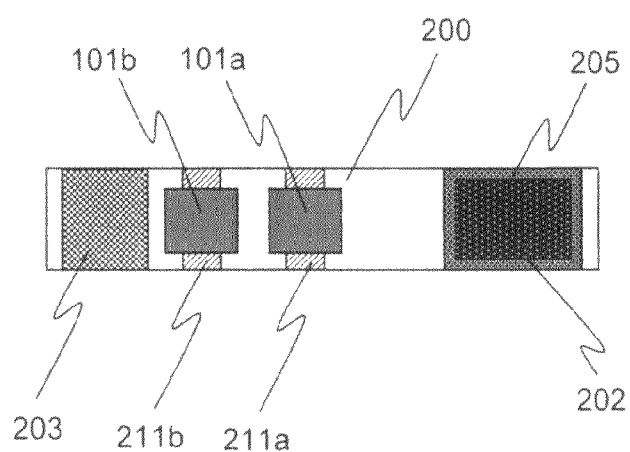
(c)
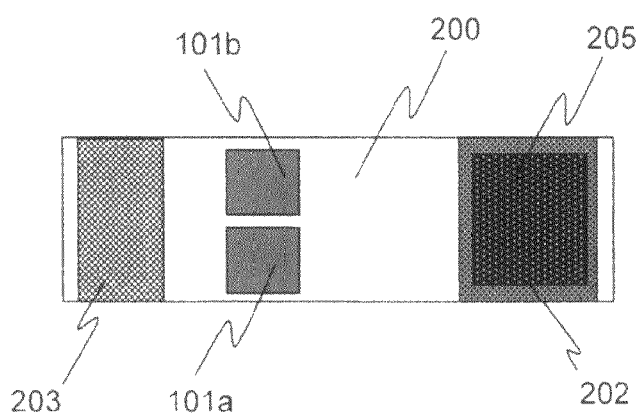

Fig. 15
(a) 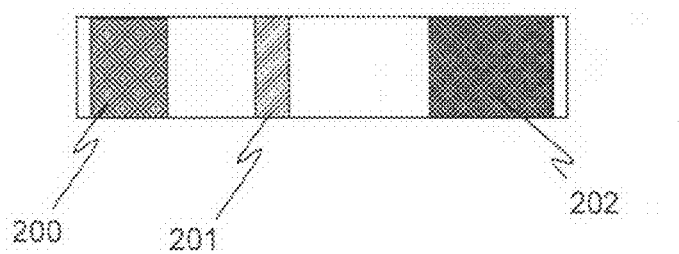
200  201  202
(b) 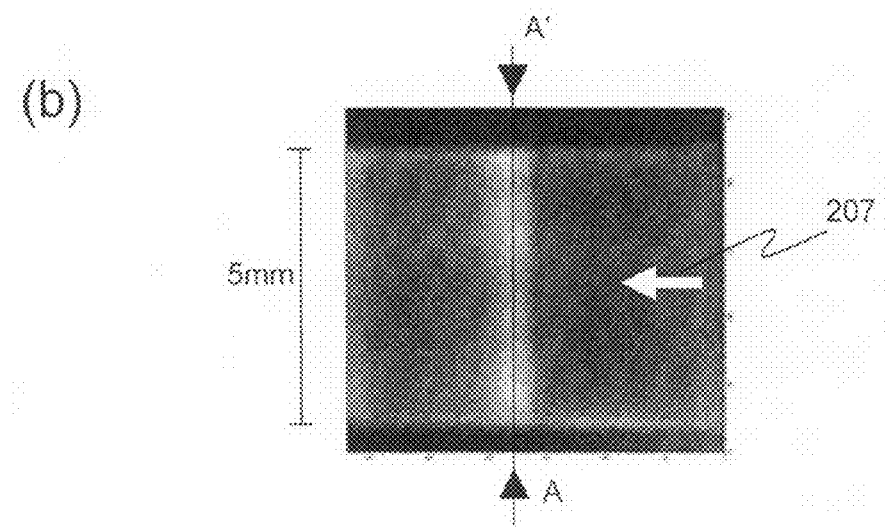
(c) 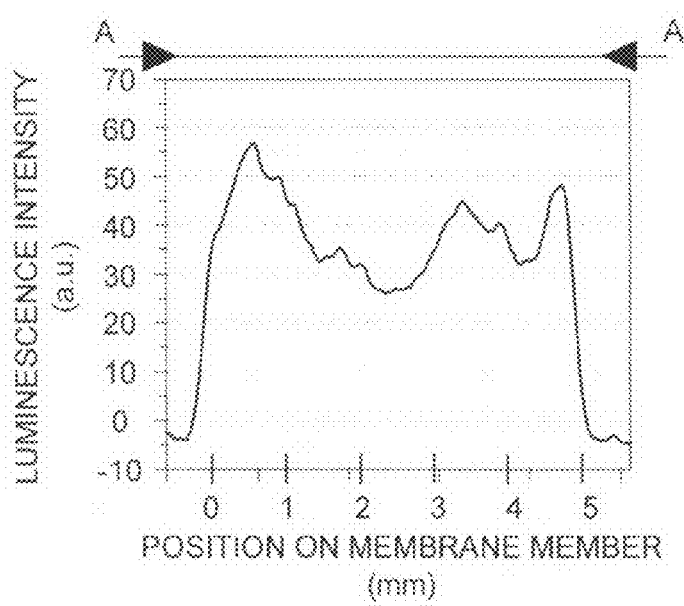

Fig. 16
(a)
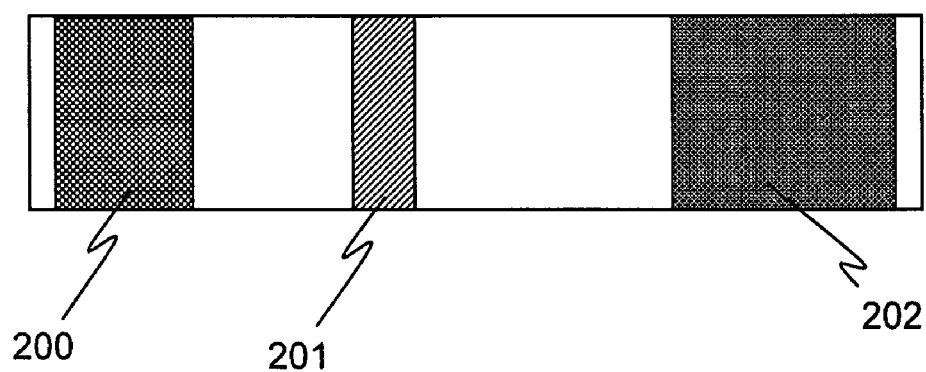
200   201   202
(b)
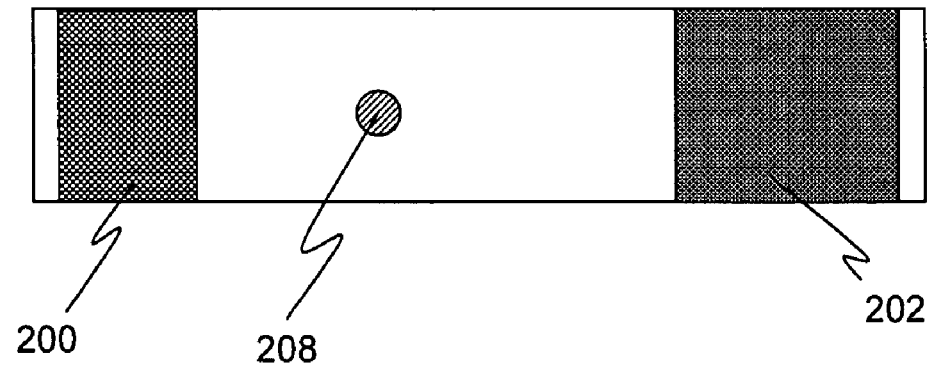
200   208   202

Fig. 17
(a)
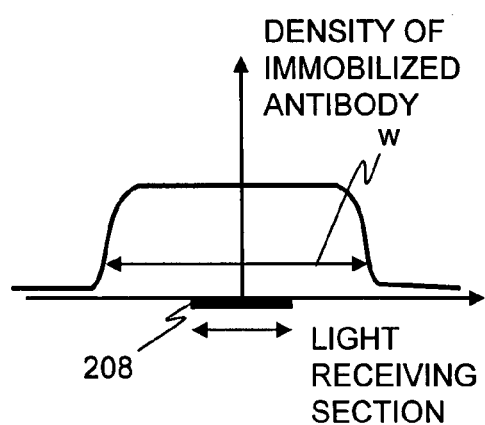
(b)
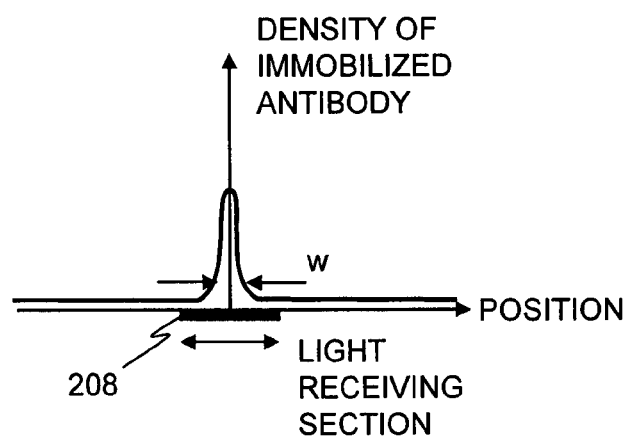
(c)
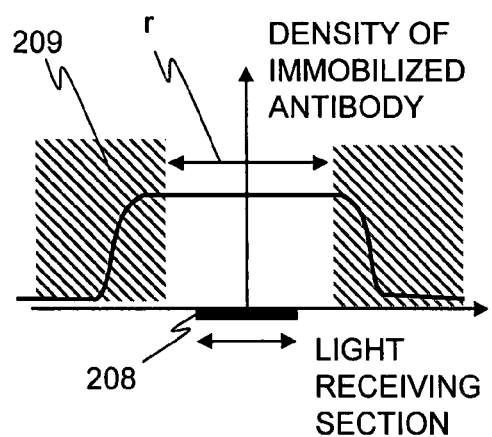
(d)
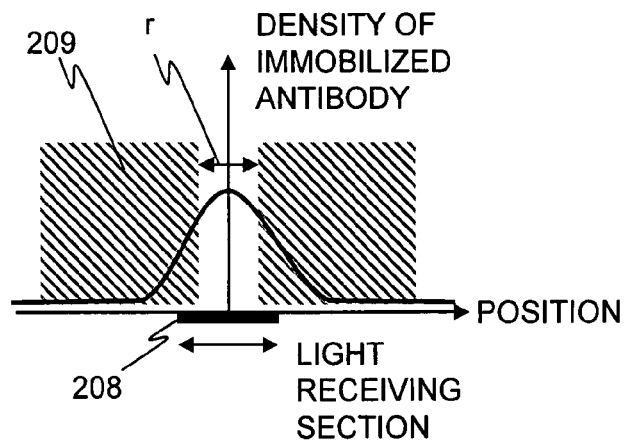

Fig. 18
(a)
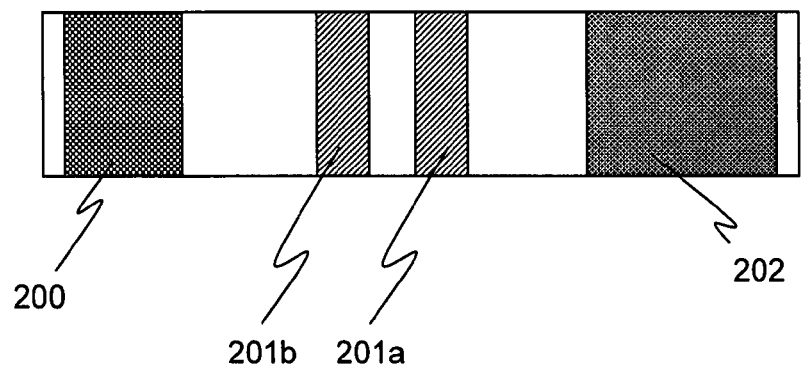
(b)
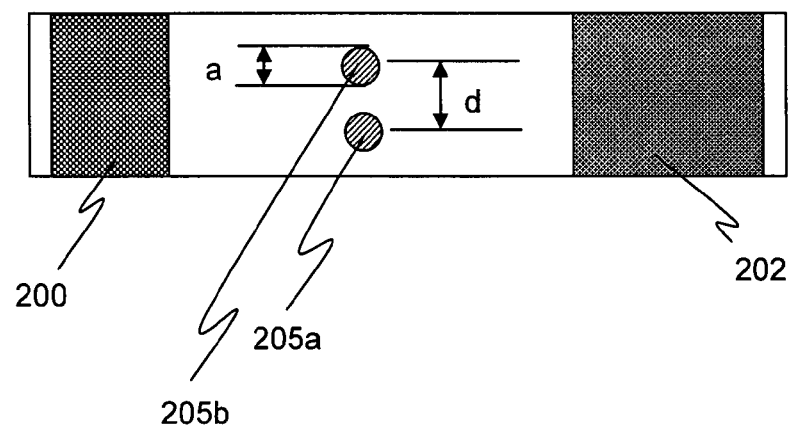
(c)
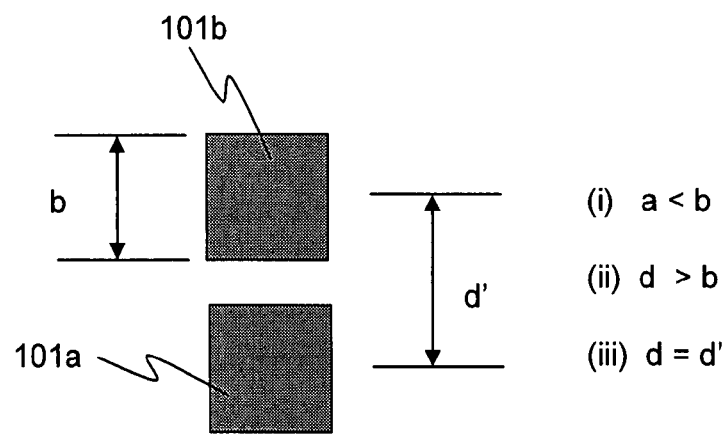
(i) a < b
(ii) d > b
(iii) d = d'

Fig. 19
(a)
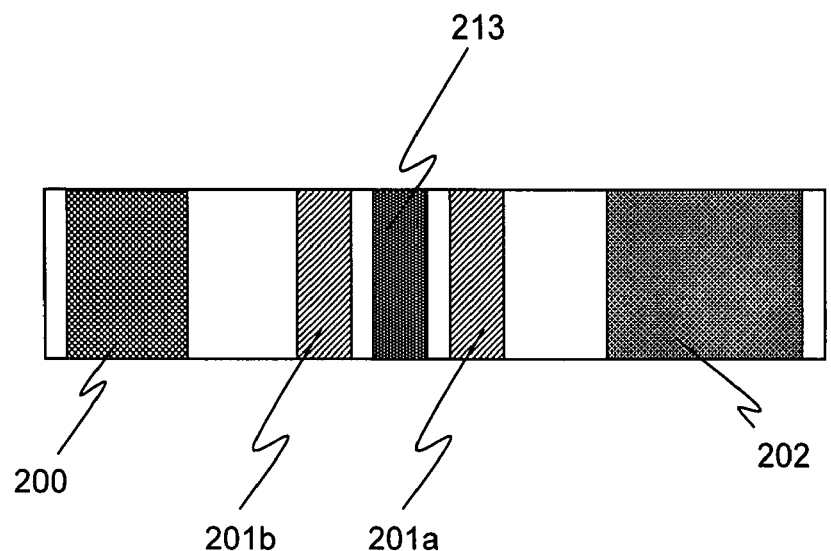
(b)
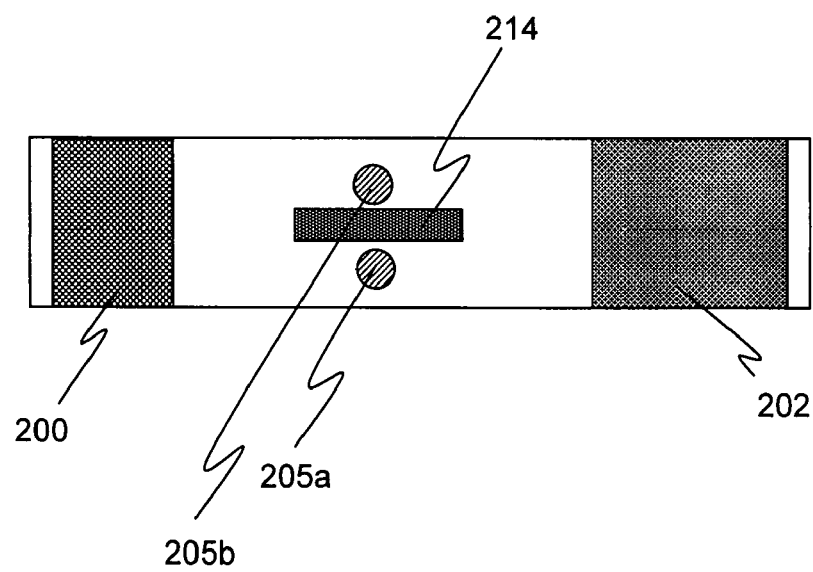

Fig. 20
(a)
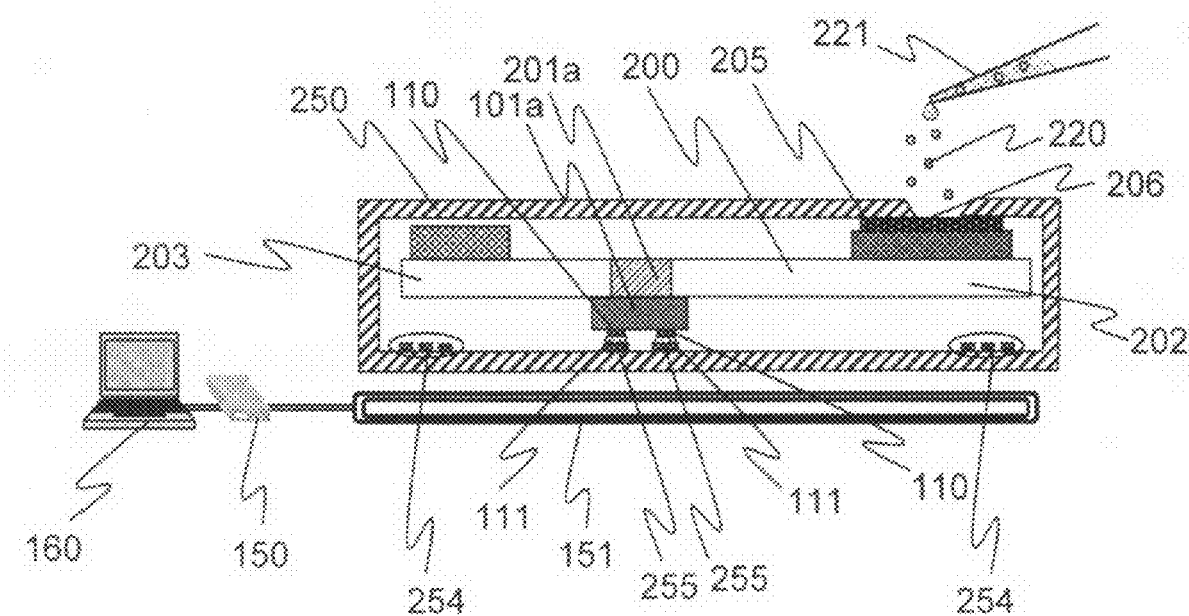
(b)
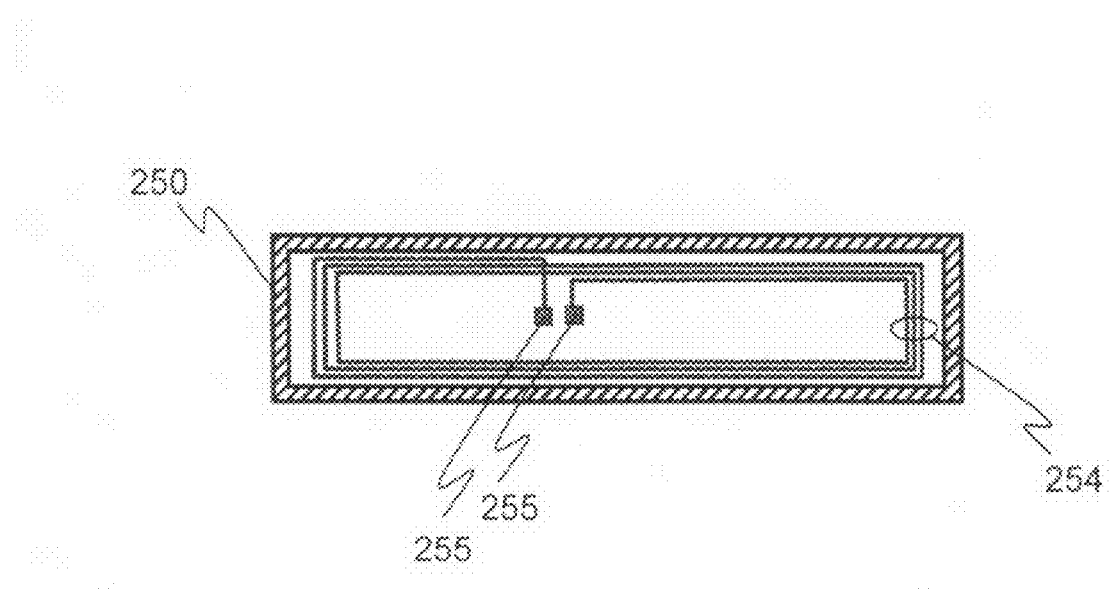

Fig. 21
(a)
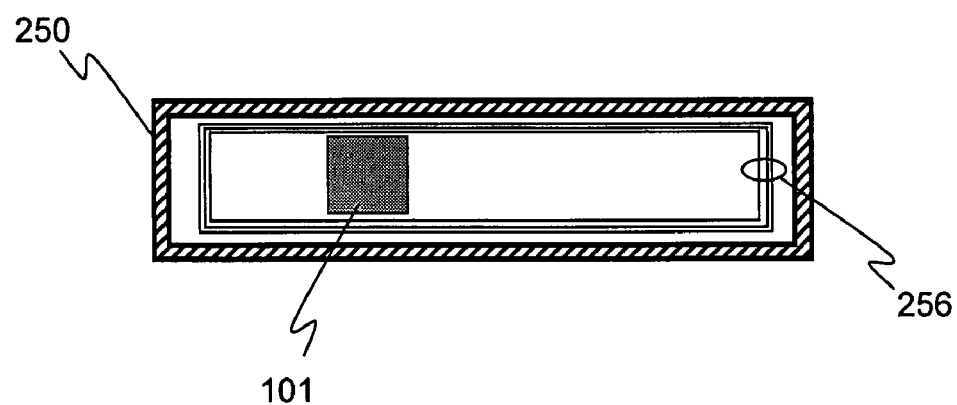
(b)
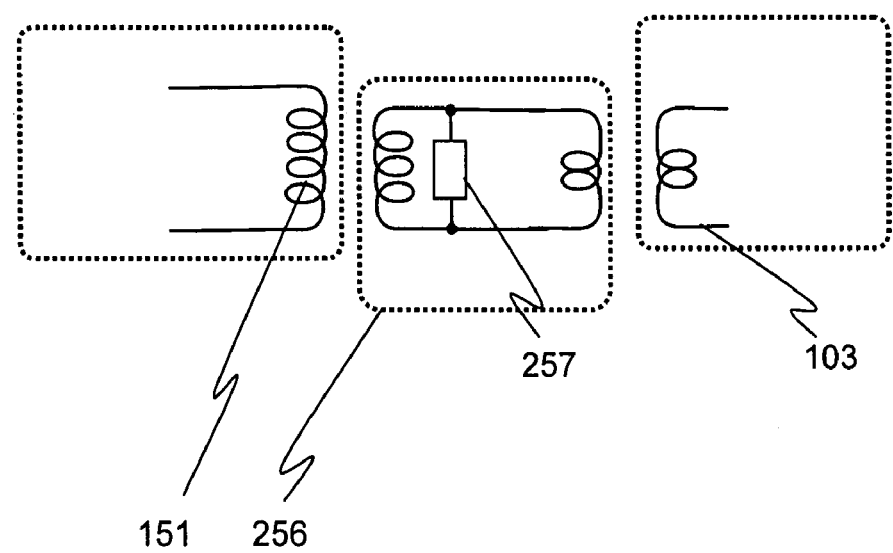

ANALYSIS KIT FOR LIVING ORGANISM AND CHEMICAL REACTION

CLAIM OF PRIORITY

The present application claims priority from Japanese application JP 2006-169146 filed on Jun. 19, 2006, the content of which is hereby incorporated by reference into this application.

BACKGROUND OF THE INVENTION

1. Field of the Invention

The present invention relates to a reaction analysis kit for analyzing biological substances, such as nucleic acids, proteins and microorganisms as well as a reaction analysis system to which the kit is applied. The reaction analysis kit and system according to the present invention allow inexpensive, simple, highly sensitive, quick analysis by applying a chemical luminescence reaction and an optical sensor chip having a wireless communication capability to immunochromatography.

2. Background Art

In analyte tests for disease markers for adult diseases, tumors and the like as well as viruses and bacteria, there have been conventionally used centralized testing apparatuses installed mostly in large hospitals and test centers from the viewpoint of cost reduction through labor saving. However, anti-influenza virus agents developed in late 1990s have required quickness in which the species of virus in question is identified at the point of care and an antiviral drug is prescribed at the same time. Inexpensive immunochromatography characterized by simplicity and acceptable sensitivity has responded to this request, resulting in rapid proliferation. POCT (Point of Care Testing) is expected to be increasingly popular in the future in various fields, such as prevention and treatment of lifestyle-related diseases including infectious diseases and cardiac infarction, and immunochromatography is expected to be one of promising POCT devices.

Immunochromatography is an inexpensive, simple technique suitable for on-site test kits. However, since immunochromatography relies on a coloring reaction visually detected, it is less sensitive than centralized test apparatuses and has difficulty in quantification. Although widely used immunochromatography test agents for influenza viruses can quickly indicate whether or not an analyte in question is infected with viruses within 15 minutes (Kawakami, et al., Influenza, 6(4), page 35, (2005)), it provides a false negative when the analyte has few viruses during the initial infection stage (Nikkei Medical, November, page 46, (2003)), so that it is desirable to improve the sensitivity (Nikkei Medical, February, page 54, (2003)). For cardiac infarction, which is one of representative lifestyle-related diseases, high correlation has been found between disease markers, such as troponin and myoglobin, and the risk of the onset of serious blood clot (E. M. Ohman, et al., N. Engl. J. Med., 335, page 1333, (1996), R. H. Christenson, et al., Clinical Chemistry, 44(3), page 494, (1998), and P. Stubbs, et al., Circulation, 94(6), page 1291, (1996)). When a patient having the risk feels chest discomfort, it is desirable to quickly perform quantitative measurement of the disease markers.

In view of the above background, there have been proposed more sensitive test apparatuses for quantitative measurement in tests of disease markers, viruses, bacteria and the like. For example, to maintain inexpensiveness and simplicity of immunochromatography and allow highly sensitive, quantitative measurement, there have been proposed methods including the steps of using an immunochromatography-based membrane, applying light to the membrane material using a light emitting diode (LED) or a laser diode (LD), and detecting the reflected light using a photodiode (PD) and digitizing the grayscale of the coloring reaction or fine particle aggregation (JP Patent Publications (Kokai) No. 2004-170217 A, No. 2005-077264 A, and No. 10-274624 A). However, since these apparatuses are configured to read reflected or transmitted light generated in immunochromatography test drugs, an optical window for the membrane needs to be provided to illuminate the membrane with the light from the LED/LD, resulting in limitation in terms of reduction in cost and size. Furthermore, since the mechanism of a coloring reaction or fine particle aggregation is used, as in conventional immunochromatography using visual inspection, it is difficult to achieve the performance of large-sized centralized test apparatuses in terms of sensitivity and the dynamic range.

Although a sensor element having a wireless communication capability and an optical sensing capability is known as a non-visual test (JP Patent Publication (Kokai) No. 2004-0101253 A), there has been no report of applying this technique to immunological test apparatuses. Even if the technique is applied to such an immunological test apparatus, there still remain problems of bulkiness and limitation of the sensitivity of the apparatus.

SUMMARY OF THE INVENTION

The present invention aims to provide a simple, inexpensive reaction analysis kit and system capable of performing highly sensitive, quantitative measurement.

To address the above challenge, the present invention proposes a novel immunochromatography-based test device. First, in the present invention, a coloring reaction or a fine particle aggregation reaction is replaced with a chemical luminescence reaction. Furthermore, visual detection is replaced with a sensor element having a wireless communication capability and an optical sensing capability. The sensor element is placed on a test section where an antibody is immobilized in such a way that it is in close contact with a membrane, and a reader coil disposed under the membrane is used to supply power to and communicate with the sensor element. The immobilized antibody is immobilized to a spot-like, limited region corresponding to the photosensitive section of the sensor element.

When the substance to be analyzed is an antigen, a sandwich method is used to perform detection and quantification, as in immunochromatography. In the sandwich method, a sample solution containing an antigen is first dripped to a sample introduction section. The antigen binds to an enzyme-conjugated antibody held in the membrane in advance and diffuses into the test section through a capillarity action. The enzyme-conjugated antibody is trapped by the immobilized antibody immobilized in the membrane in advance with the antigen sandwiched between the enzyme-conjugated antibody and the immobilized antibody, so that the enzyme is localized. The enzyme localized in the test section causes a luminescence substrate introduced after the conjugated antibody solution and the sample solution to emit light. The sensor element then detects the luminescence in a realtime manner.

In the present invention, a simpler, lower-cost reaction analysis kit can be configured based on immunochromatography. Use of chemical luminescence eliminates an excitation light source required in the case of a fluorescence measurement, so that only a photo detecting element is necessary. In this way, the effect of excitation light scattering is eliminated, resulting in a reduced background signal. Furthermore, the simplified detection mechanism easily allows reduction in cost and size.

Specifically, bringing the sensor element in close contact with the light emitting portion of the membrane provides three advantages: a first advantage is that the optical coupling efficiency is improved by bringing the optical sensor in close contact with the light emitting portion. As for the system by conventional technology, a signal, for example light absorbance, is measured by a built-in sensor in a measurement unit, so optics for focusing the signal light is required. On the other hand, because the wireless sensor element can directly contact the target, coupling efficiency between the sensor and target is high, resulting in high sensitivity without any optics, a second advantage is that change in an electric field caused by the sample solution that diffuses through the membrane and hence variation in output from the optical sensor can be used to detect the diffusion of the sample solution, and a third advantage is that bringing the sensor in close contact with the light emitting portion eliminates the need for a component support structure, allowing the apparatus to be substantially simplified.

Use of the wireless communication to send data from the sensor element provides five advantages: a first advantage is that there is no need to provide wiring lines and electrodes for extracting a signal from the sensor element, allowing reduction in cost and size of the reaction detection kit, a second advantage is that no contact is required to couple the sensor element to external devices, such as a reader, resulting in improvement in reliability, a third advantage is that an anti-collision control capability in which one reader coil handles a plurality of sensor elements provides design flexibility in which only changing the number and position of the sensor elements can handle a change in number of measurement items and change in position and number of spots of immobilized antibodies on the membrane, and a fourth advantage is that since inductive coupling between the sensor element and the reader coil supplies power to the sensor element, even when a plurality of sensor elements are used, the sensor elements can be electrostatically separated from the reader and another sensor elements, so that the sensor elements are floated electrostatically and can minimize the effect of electrostatic potential on the substance to be analyzed. The fifth advantage is a "closed environment", a sample can be measured in fully sealed package. So this invention can offer such a measurement system with no contamination to the sample or no infection from the sample.

Immobilizing antibodies to a limited region of the membrane, on which the optical sensor of the sensor element is placed, provides two advantages: a first advantage is that when the immobilized antibody pattern is formed, a fixed amount of the immobilized antibody can be discharged from a nozzle to immobilize a predetermined amount of antibody in a highly reproducible manner, and a second advantage is that immobilizing the antibody only to the limited region can reduce the loading amount of expensive antibody.

As described above, according to the present invention, there is provided a low-cost, compact, highly-sensitive, reliable reaction analysis kit with a simple structure capable of flexibly handling various analyses.

BRIEF DESCRIPTION OF THE DRAWINGS

FIG. 1 shows the configuration of the reaction analysis kit in Example 1;

FIG. 4 shows the principle of the operation of the sensor element;

FIG. 5 shows optical coupling between the sensor element and luminescence in a membrane;

FIG. 7 shows an example of a structure that prevents light from entering through a sample introduction section;

FIG. 8 shows a structure that collectively measures luminescence from an antibody immobilized section and a blank region;

FIG. 11 explains an example of a structure for handling a plurality of substances to be analyzed;

FIG. 15 explains non-uniformity of chemical luminescence;

FIG. 16 explains an example of a spot-like pattern on which antibody is immobilized;

FIG. 17 explains an example of how to produce a spot-like pattern on which antibody is immobilized;

FIG. 18 explains an example of a structure for handling a plurality of substances to be detected;

FIG. 19 explains an example of a structure for reducing crosstalk;

FIG. 20 explains an example in which a sensor element-side coil is disposed in a shielding container; and FIG. 21 explains an example in which a relay coil is disposed in the shielding container.

DETAILED DESCRIPTION OF THE PREFERRED EMBODIMENTS

Figure 2:
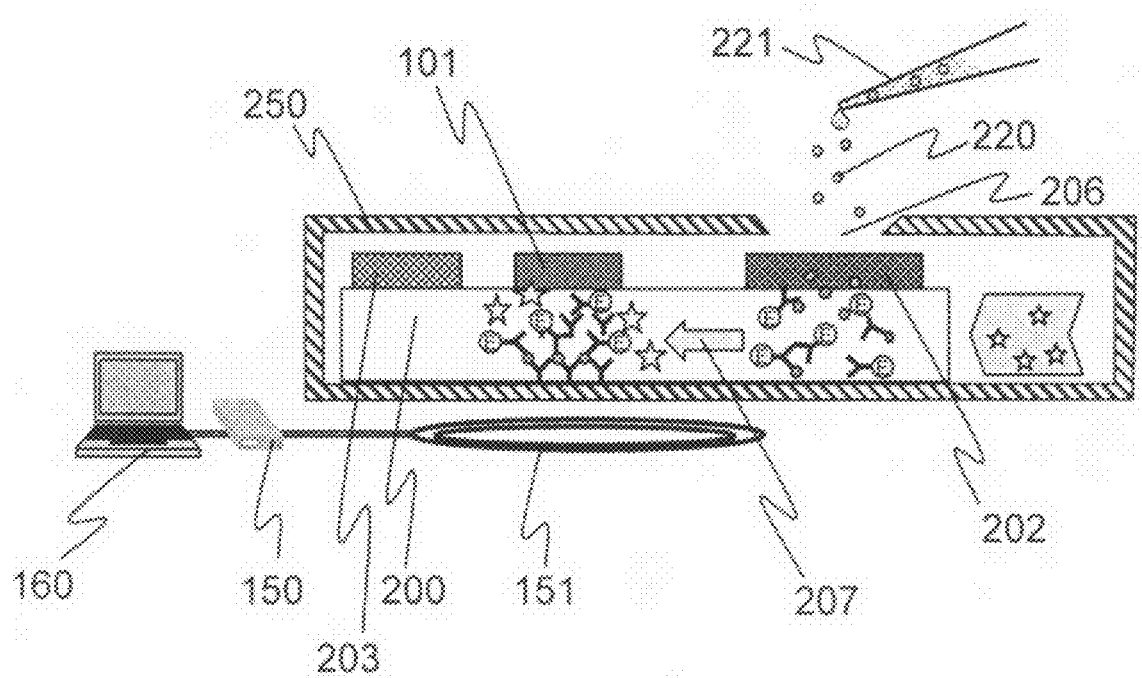
FIG. 2 shows an example of chemical luminescence mechanism in the reaction analysis kit of the present invention.

The reaction analysis kit according to the present invention includes a first labeled antibody that specifically binds to a substance to be analyzed, a reagent that reacts with the labeling substance and emits light, and a reaction detection plate. The reaction detection plate has a) a membrane, b) a first antibody impregnated section that is disposed such that it faces the membrane and holds the first antibody, c) a second antibody immobilized section that is provided in part of the membrane and has an immobilized second antibody, the second antibody specifically binding to the substance to be analyzed, and d) a sensor element that is disposed such that it faces the second antibody immobilized section and includes a light detector and a signal transceiver. The sensor element detects the light generated in the reaction between the substance to be analyzed and the antibody.

From the viewpoint of sensitivity, the sensor element is preferably closer to the second antibody immobilized section (at least within 200 μm), more preferably in close contact therewith.

In an embodiment, the reaction detection plate is housed in a shielding container in order to eliminate the effect of external light.

The sensor element may be disposed on the same side as the first antibody impregnated section with respect to the membrane (upper side against the gravity) or may be disposed on the opposite side of the membrane to the first antibody impregnated section (lower side along the gravity). The sensor element disposed on the opposite side to the first antibody impregnated section is closer to a reader coil, allowing more stable communication to be achieved.

In the kit described above, it is preferable that the second antibody immobilized section is shaped into a spot, that is, substantially circular, and the center of the second antibody immobilized section faces the center of the light detector. The area of the light detector on the side facing the second antibody immobilized section may be the same as that of the second antibody immobilized section on the side facing the light detector, or one of the areas may be greater than the other.

If the second antibody immobilized section has a region that does not face the light detector, the region has preferably undergone an antibody inactivation process. This can eliminate measurement errors to provide accurate detection.

When the center of the light detector faces the center of the second antibody immobilized section, and the diameter of the light detector is at least 10 μm but smaller than or equal to 2 mm, a region apart from the center of the second antibody immobilized section by 2.5 mm or greater has preferably undergone an antibody inactivation process.

The analysis kit according to the present invention preferably has one of the following components in the shielding container in order to reliably block light from entering the sensor element: a projection that fills the gap between the membrane and the shielding container and a light-blocking filter having a visible light transparency of 1% or lower.

In the analysis kit according to the present invention, the number of the sensor element and the second antibody immobilized section is not limited to one, but may be two or more. For example, when two or more substances to be analyzed are analyzed, a plurality of second antibody immobilized regions and a plurality of sensor elements are required for the respective substances to be analyzed. Alternatively, by disposing a second sensor element that faces the region other than the antibody immobilized region and calculating the difference in photodiode output between the first and second sensor elements, signal components other than chemical luminescence can be removed.

The analysis kit according to the present invention may have a mirror (reflective mirror) disposed such that it covers part or all of the second antibody immobilized section. In this way, the effect of light scattering can be minimized.

The shielding container may have a guiding structure for defining the position where the sensor element is disposed.

Furthermore, part of the membrane has a light absorbing region for preventing crosstalk.

The present invention also provides a reaction system that uses the reaction analysis kit. The system includes i) the reaction detection plate described above, ii) a shielding container that houses the reaction detection plate, iii) a reader coil disposed outside the shielding container, the reader coil transmitting and receiving a signal to and from the sensor element and supplying power to the sensor element, iv) a reader that performs demodulation/modulation, decoding/coding and amplification of the signal, and v) a processor for executing an application program that controls the sensor element.

A sensor element-side coil may be disposed in the shielding container. Furthermore, a relay coil that inductively couples the sensor element-side coil to the reader coil may be disposed.

The analysis kit and the system according to the present invention are based on immunochromatography and employ an enzyme-based chemical luminescence reaction instead of fine particle aggregation or an enzyme-based coloring reaction typically and frequently used. Furthermore, visual detection is replaced with an optical sensor-equipped sensor element with a communication capability. The sensor element is then placed on a test section where an antibody is immobilized in such a way that the sensor element is in close contact with the membrane, detects a luminescence signal, and transmits the detection result to the reader outside the shielding container in a wireless manner. The membrane, the sensor element, the antibody and the enzyme that modifies the antibody are housed in the shielding container for convenience of storage and handling as well as for blocking external light. The reader coil disposed outside the shielding container supplies power to and communicates with the sensor element. The sandwich method is used to detect and quantify a target antigen, as in immunochromatography shown in FIG. 1. In the sandwich method, a sample solution containing an antigen is first dripped to the sample introduction section. The antigen binds to an enzyme-conjugated antibody held in the membrane in advance and diffuses into the test section through a capillarity action. The enzyme-conjugated antibody is trapped by an immobilized antibody with the antigen sandwiched therebetween, so that the enzyme is localized. The enzyme localized in the test section causes a luminescence substrate introduced after the conjugated antibody solution and the sample solution to undergo a luminescence reaction. When the enzyme is alkaline phosphatase, for example, 1,2-dioxetane-based luminescence substrate can be used. The sensor element then detects the luminescence reaction in a realtime manner.

EXAMPLE 1

A first example of the present invention will be described with reference to FIGS. 1 to 4. A shielding container 250 houses a dry membrane 200 where an antibody is immobilized. Examples of the material of the membrane include nitrocellulose, nylon, and PVDF (polyvinylidene-Fluoride). Among them, nitrocellulose is frequently used because an antibody can be easily immobilized. The sandwich method is used to detect and quantify a substance to be analyzed, as in immunochromatography. An antibody that specifically binds to a target antigen is immobilized to a portion (test section) 201 of the membrane 200, as shown in FIG. 2. A sample extracted from blood or the like is dripped to a sample introduction section 206 above the membrane 200 through an opening provided in the shielding container 250.

An enzyme-conjugated antibody 224 specific to the antigen of the substance to be analyzed is held in advance in a sample pad 202 placed in the sample introduction section 206 above the membrane 200. Examples of the enzyme that modifies the antibody include alkaline phosphatase, peroxidase, β-galactosidase and luciferase, which catalyze chemical luminescence. Among them, alkaline phosphatase and peroxidase are easily used from the viewpoint of substrate stability and sensitivity. A substance to be measured (antibody in this case) 220 in the sample solution binds to the enzyme-conjugated antibody 224 and reaches the test section 201 through a capillary action. The enzyme-conjugated antibody 224 is trapped by an immobilized antibody 222 in such a way that the antigen 220 is sandwiched therebetween, and a chemical luminescence substrate 225 emits light through the effect of the enzyme that have gathered. When no antigen 220 is present in the sample solution, no enzyme-conjugated antibody 224 is trapped by the immobilized antibody 222 and hence no light is emitted.

Figure 3:
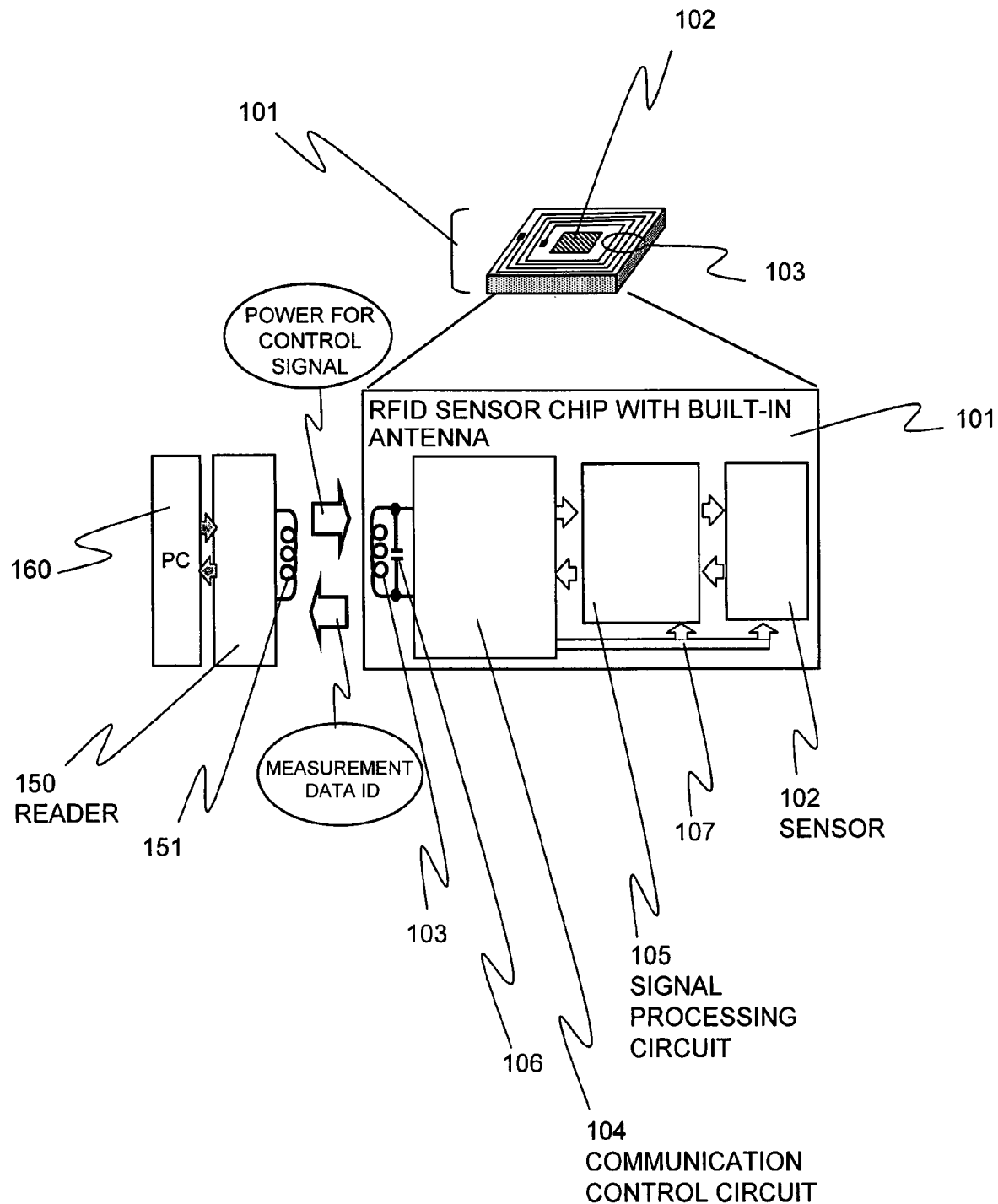
FIG. 3 shows an example of the configuration of a sensor element.

To measure the chemical luminescence, an optical sensor-equipped sensor element with a wireless communication capability shown in FIG. 3 was applied. The sensor element (see JP Patent Publication (Kokai) No. 2004-0101253 A) is composed of a sensor 102, a signal processing circuit 107, a communication control circuit 104, a chip coil 103, and a resonance capacitor 106. In FIG. 2, the optical sensor is applied to detect the chemical luminescence. An optical signal obtained from the optical sensor is amplified and digitized in the signal processing circuit 107, coded and modulated in the communication control circuit 104, and transmitted from the chip coil 103.

As shown in FIG. 3, although the function blocks are desirably integrated on one silicon substrate, the circuit blocks may be separately fabricated and assembled into a module.

Although a small-sized battery can be used as the power supply for the sensor element, it is desirable from the viewpoint of reduction in cost and size to employ a form in which inductive coupling between a reader coil 151 and the chip coil 103 shown in FIG. 4 is used to supply power from a reader 150. The sensor element 101 is in close contact with the membrane 200 above the test section 201 where the antibody is immobilized. In this example, the reader coil 151 was disposed under the shielding container 250 in order to supply power to and communicate with the sensor chip. The reader coil 151 connected to the reader 150 supplies power to the sensor element 101 and transmits and receives signals to and from the sensor element. The reader performs demodulation/modulation and decoding/coding of the signals. Examples of a carrier wave used for power supply and signal transmission/reception include an alternating magnetic field, an alternating electric field and an electromagnetic wave. The frequency of the carrier wave can be 120 to 500 kHz, 13.56 to 50 MHz, 500 to 950 MHz, 2.5 to 5 GHz or intermediate values in these ranges. Examples of the demodulation/modulation method include ASK (Amplitude shift keying) and FSK (Frequency shift keying). Examples of the coding method include the Manchester, NRZ (Non return to zero), pulse position, and mirror schemes. The reader 150 is controlled by a processor 160.

A description will now be made of the case where hCG (human chorionic gonadotropin; ROHTO Pharmaceutical Co., Ltd., Product No. R-505, mouse-derived cells), a protein used for pregnancy tests and tumor markers, is selected as the substance to be analyzed. The membrane was a porous membrane made of nitrocellulose (Whatman PRIMA85), and the alkaline phosphatase (AP)-conjugated first antibody was anti-hCG IgG (MedixBiochemica, clone code 5008, mouse-derived monoclonal anti-hCG) that was AP-conjugated using an AP labeling kit (Dojindo, Alkaline Phosphatase Labeling Kit-SH). The hCG dripped through the sample introduction section and the AP-conjugated antibody 224 diffused through the membrane 200 and directly bound to the immobilized antibody in the test section 201, so that the AP was localized in the test section 201. Subsequently, the sensor element 101 detected a free luminescence substrate (Tropix CDP-Star™).

The sensor element uses inductive coupling between the sensor element and the reader coil 151 to perform power supply and communication, as shown in FIG. 4(*a*). The current induced in the coil 103 on the sensor element decreases as the communication distance increases, as shown in FIG. 4(*b*), and becomes equal to the current (800 μA) necessary for the operation of the sensor element when the communication distance is 1 mm. That is, to drive the sensor element, the distance d between the reader coil 151 and the sensor element 101 needs to be 1 mm or smaller. This means that the thickness of the material that forms the lower side of the shielding container must be 1 mm or smaller.

A description will now be made of assembly of the sensor element 101, the membrane 200 and the shielding container 250. In the configuration shown in FIG. 1, letting c be the thickness of the sensor element 101, t be the thickness of the uncompressed membrane 200, and d be the distance between the upper and lower inner walls of the shielding container, the thicknesses of the respective components are designed to satisfy d<c+t. In this way, the components can be assembled without using any adhesive or special connecting means. A filler, such as an adhesive and a sealant, may be used to bring the sensor element 101 and the membrane 200 in close contact. In this case, however, the filler needs to be stable toward the sample solution and the luminescence substrate solution. From the viewpoint of the optical coupling efficiency between the membrane and the sensor element, the refractive index of the filler is desirably 1.3 to 1.8.

The reaction analysis kit according to the present invention is provided in a disposable form in which the sensor element, the membrane and the shielding container are integrated. It is thus possible to bring the sensor element and the membrane in close contact in the shielding container. On the other hand, in the case of a conventional reaction analysis kit, the membrane and the case for housing the membrane are disposable, while the detector is separately mounted for repeated use. A window member is therefore necessary to protect the detector, so that a space between the light source and the light receiving section must be provided. The impact of the distance h between the membrane 200 and the light receiving section of the sensor on the optical coupling efficiency will now be discussed. The optical coupling was calculated using the solid angle shown in FIG. 5. In a conventional installable detection system, the distance between the light receiving section and the membrane necessary to dispose the protection window or the like is about 5 mm. The size of the light receiving section of the sensor used in conventional methods is about 1 mm by 1 mm, and the optical coupling efficiency, which is the probability of the light emitted from the light source being trapped (4 Ωab/4π), is 0.04 as shown in the left table of FIG. 5(*c*). In the reaction analysis kit based on the present invention to which the sensor element (the size of the light receiving section: 0.16 mm by 0.31 mm) is applied, the optical coupling efficiency is 0.176 when the distance h between the sensor element and the light source is 0.2 mm, as shown in the right table of FIG. 5(*c*). The optical coupling efficiency conventionally achievable (5.17 when h=0.2) can therefore be improved by one order or greater.

EXAMPLE 2

Figure 6:
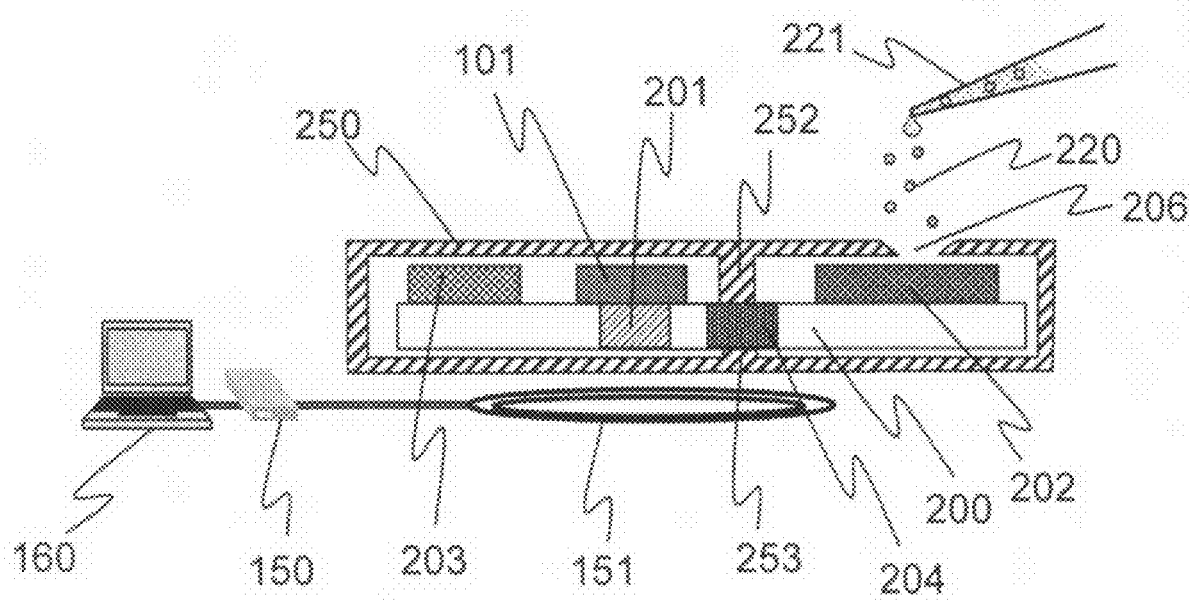
FIG. 6 shows an example of a structure that prevents light from entering through a sample introduction section.

As a second example, a description will be made of the case where a projection is provided in the shielding container and an incoming light absorber is provided in the membrane in order to prevent external light from entering with reference to FIG. 6.

To accurately measure chemical luminescence using the sensor element, it is necessary to provide means for preventing external light from entering. In the reaction analysis kit according to the present invention, since the opening is provided in the shielding container 250 at the sample introduction section 206 in order to introduce a sample into the membrane 200, it is desirable to block external light from entering through this opening. First, a projection is therefore provided in the shielding container 205 in such a way that the projection fills the gap between the shielding container and the membrane. The projection to be provided includes at least one of a projection 252 extending from the inner upper surface of the shielding container and a projection 253 extending from the inner lower surface. In this way, it is possible to block the light that enters through the sample introduction section and then propagates through the gaps between the membrane 200 and the inner walls of the shielding container 250. Letting d be the distance between the upper and lower inner walls of the shielding container and t be the thickness of the membrane, the height s1 of the upper projection 252 and the height s2 of the lower projection 253 must satisfy the following equation:

$$s1+s2>d+t$$

An incoming light absorbing dye dispersed in part or all of a region 204 sandwiched between the upper projection 252 and the lower projection 253 can prevent the light propagating through the membrane 200 from reaching the sensor element 101. The dispersed dye should not prevent dispersion of the conjugated-antibody, the antigen and the luminescence substrate. Examples of the dye used for a cellulose-based membrane include Methylene Blue, Indigo and Toluidine blue. Examples of the dye used for a PVDF (PolyVinyliDene Fluoride)-based membrane include 1,4-diaminoanthraquinone. Examples of the dye used for a nylon-based membrane include CI Mordant Black 3.

EXAMPLE 3

As a third example, a description will be made of the case where a light-blocking filter is used with reference to FIG. 7.

This example aims to prevent light from entering through the opening in the shielding container 250 above the upper part of the sample introduction section 206, as in Example 2. A light-blocking, solution-permeable filter 205 is disposed inside the shielding container 250 such that it covers the opening in the container. Examples of the material of the light-blocking filter include glass fibers, nitrocellulose, PVDF and nylon. For example, the light-blocking property can be imparted by mixing the dye that stains the membrane shown in Example 2 with the light-blocking filter or adsorbing the dye on the surface of the light-blocking filter depending on the material of the light-blocking filter.

EXAMPLE 4

As a fourth example, a description will be made of the case where a second sensor element is used with reference to FIG. 8.

FIG. 8(a) shows the cross-sectional structure, and FIG. 8(b) shows the plan view of the membrane and the surrounding components. In addition to a first sensor element 101a disposed on the area 201 where an immobilized antibody is immobilized, a second sensor element 101b is disposed on an area of the membrane 200 other than the area 201 where the immobilized antibody is immobilized. By calculating the difference in optical sensor output, that is, photodiode output, between the first sensor element 101a and the second sensor element 101b to remove signal components other than the chemical luminescence, the chemical luminescence reaction can be analyzed with high accuracy.

EXAMPLE 5

Figure 9:
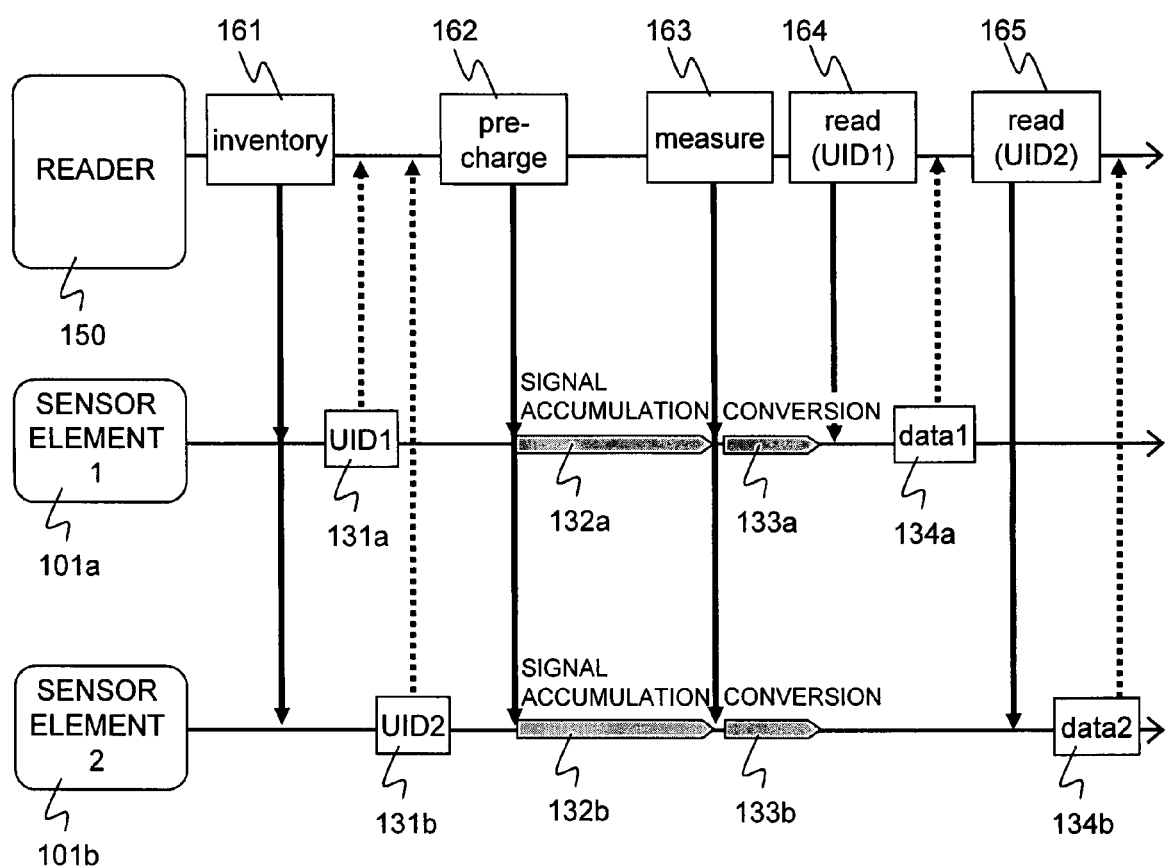
FIG. 9 explains a sequence for driving a plurality of sensor elements.

As a fifth example, a description will be made of a method for collectively controlling a plurality of sensor elements with reference to FIG. 9.

In driving sensor elements, commands from the reader 150 perform various control operations, such as identifying a plurality of sensor elements, controlling the equipped sensors, and reading sensor outputs. Each of the sensor elements used in this example has a unique identifier (UID) (see JP Patent Publication (Kokai) No. 2004-0101253 A). The present reaction test system based on use of such sensor elements is characterized in that two types of command modes sent from the reader to the sensor elements are properly used to achieve accurate measurement timing synchronization among the plurality of sensor elements. A measurement sequence will be described below with reference to FIG. 9.

In driving an optical sensor, a signal is read by sequentially sending the following commands: (i) an inventory command 161 for detecting sensor elements present in a communicable range, (ii) a pre-charge command 162 for charging each photodiode to a predetermined voltage in order to drive the photodiode in a charge accumulation mode, (iii) a measure command 163 for converting the photodiode voltage into a digital signal following the pre-charge and a lapse of a predetermined signal accumulation period (Tss), and (iv) read commands 164 and 165 for reading output signals (digital signals) of the sensors. The inventory command is broadcast from the reader without identifying individual sensor elements, and each of the sensor elements that receives the inventory command 161 returns its UID to the reader at a specific timing (time slot) according to the UID. In FIG. 9, UID1 131a from the first sensor element 101a and UID2 131b from the second sensor element 101b are sent to the reader in response to the inventory command 161. The pre-charge command 162 is also broadcast from the reader without identifying individual sensor elements (non-addressing mode), and each of the sensor elements charges the photodiode and enters the signal accumulation mode. The measure command 163 is also broadcast from the reader without identifying individual sensor elements (non-addressing mode), and an ADC (Analog to Digital Converter) digitizes the cathode voltage of the photodiode that has been changed by the effect of incident light. The digitized measurement value is latched in each of the sensor elements. The read commands 164 and 165 are sent to respective sensor elements according to their UIDs (addressing mode), and read the digital values data1; 134a and data2; 134b, which are the photodiode outputs latched in the sensor elements.

When a command is executed in the addressing mode and each of the sensor elements is accessed in the collective control of a plurality of sensor elements, sending the command to each sensor element requires 10 ms to 300 ms, which prevents the measurement timings for the plurality of sensor elements to accurately coincide with each other. By properly using commands in the non-addressing mode and the addressing mode described above, it is possible to synchronize the measurement timings in an accurate manner. To detect a minute signal in the chemical luminescence measurement according to the present invention, the signal accumulation period may be set to a large value, that is, 100 milliseconds to 20 seconds. In this case, to remove common mode noise generated in the measurement period, it is necessary to accurately synchronize the measurement timing for the first sensor element for signal detection with that of the second sensor element for reference. The method in this example allows the measurement timings for a plurality of sensor elements to accurately coincide with each other.

EXAMPLE 6

Figure 10:
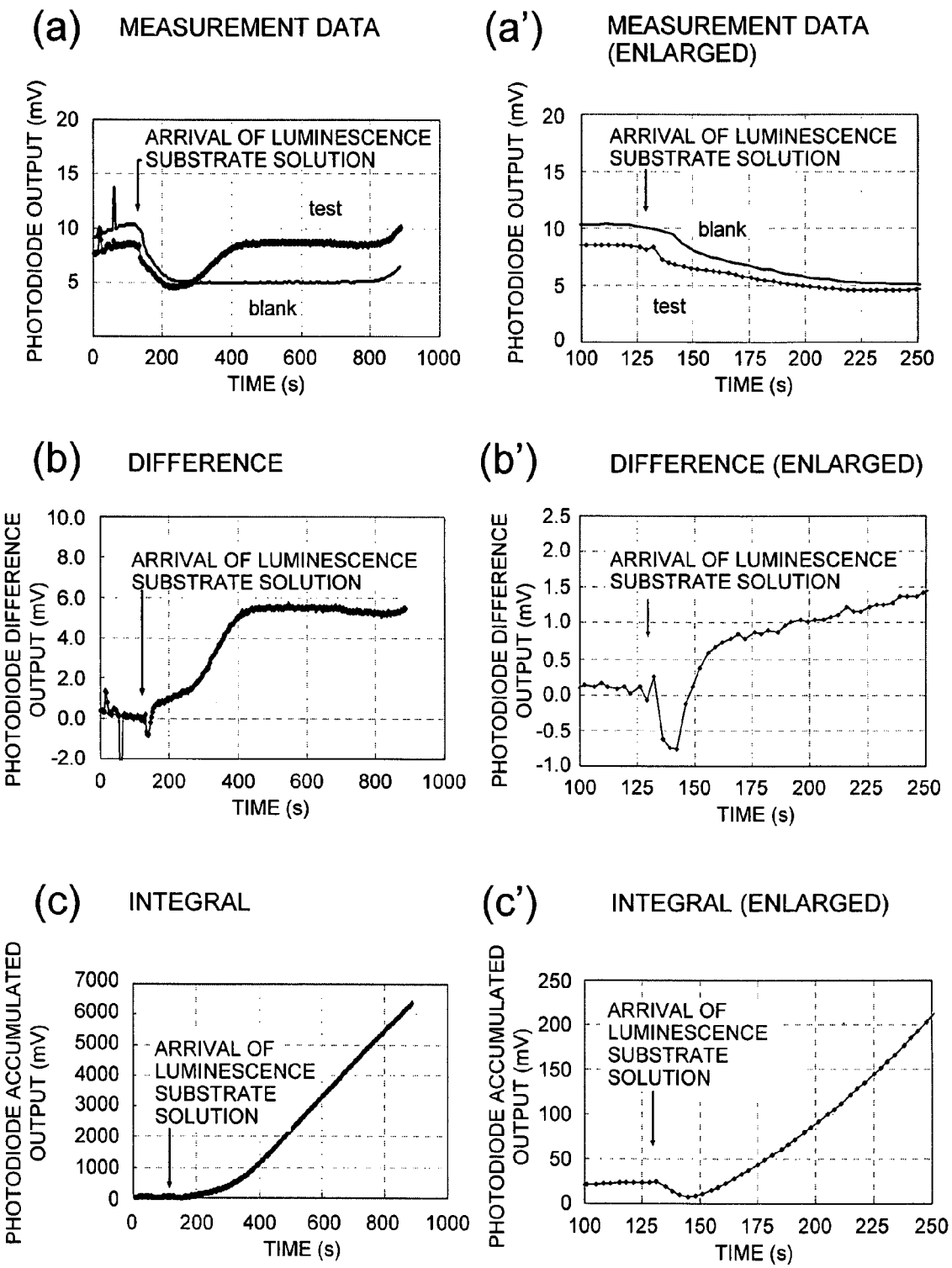
FIG. 10 explains an example of a method for processing measurement data from sensor elements.

As a sixth example, FIG. 10 shows the results measured according to Examples 4 and 5. The horizontal axis represents time and the vertical axis represents the photodiode output values sent from the sensor elements. The character "test" represents the result obtained by using the sensor element 101a to measure the signal from the region (test section) 201 where the immobilized antibody is immobilized, and the character "blank" represents the result obtained by using the sensor element 101b to measure the signal from the region where no immobilized antibody is present. The sample is hCG, the concentration of which is 100 ng/ml, and the dripped amount is 30 µl.

Decrease in output is observed for test and blank around at 130 seconds, illustrating that the sample solution has reached the sensor elements. The membrane used in this measurement (Whatman PRIMA85) has a solution permeating speed of 0.38 to 0.53 mm/s, and the distance from the dripping point to the antibody immobilized region 201 is 3 mm. The time when the solution was dripped therefore corresponds to 122 to 124 seconds in the graph. To check whether the amount of the dripped sample solution was enough and whether impurities and the like in the solution did not prevent diffusion, it is important, among various items to be checked for judging whether the reaction analysis process has been normally done, to detect that the solution has reached the antibody immobilized region. In the present invention, whether or not the solution has reached can be detected by reading the in-phase change in the blank and test photodiode outputs. This method requires no special mechanism and hence is effective to reduce the size and cost of the reaction analysis kit.

FIG. 10(a) shows that chemical luminescence rises around at 250 seconds and reaches a plateau after a lapse of 400 seconds. FIG. 10(a)' is an enlarged view showing the behavior at the time when the solution reaches the antibody immobilized section. Detailed analysis of the figure reveals that the difference between blank and test keeps getting smaller immediately after the arrival of the solution, but the rising edge of the chemical luminescence cannot be positively judged. FIGS. 10(b) and 10(b)' show the difference D between test and blank. The figures show that the chemical luminescence rose after a lapse of 150 seconds at the latest. FIGS. 10(c) and 10(c)' show the integral I of the difference between test and blank with respect to time. I(T) is defined by the following equation, where Tss represents the signal accumulation period in one measurement. In the measurement shown in FIG. 10, Tss is 500 ms.

$$I(T)=\int_0^T (D(T)/Tss)dT$$

By thus performing the integral operation, variation in data decreases and the rising edge of the chemical luminescence can be read in a more accurate manner.

As shown in the present example, the variation in in-phase output of the first and second sensor elements can be used to detect the state of diffusion of the sample solution and the luminescence substrate solution, and the difference or the integral of the difference in output between the first and second sensor elements can be calculated to accurately measure the chemical luminescence.

EXAMPLE 7

As a seventh example, a description will be made of the case where two or three, or even more substances to be analyzed are detected with reference to FIG. 11.

As shown in FIGS. 11(a) and 11(b), regions 211a and 211b where antibodies that specifically bind to a plurality of substances to be analyzed are immobilized are provided in the membrane, and the sensor elements 101a and 101b are provided in such a way that they are in close contact with the respective regions. Since the sensor elements transmit signals by wireless communication, it is necessary only to dispose sensor elements within the communication field of the reader coil 151. There is no need to newly design wiring lines, electrodes and a collection optics, allowing plural substances to be analyzed to be handled.

FIG. 11(c) shows another example in which two or three, or even more substances to be analyzed are detected. In FIG. 11(b), the antibody immobilized regions 211a and 211b are sequentially disposed in the direction in which the sample solution diffuses, while in FIG. 11(c), the two antibody immobilized regions are disposed immediately under the sensor elements 101a and 101b and on a line perpendicular to the direction in which the sample solution diffuses. In this layout, two types of substances to be analyzed diffuse through the same distance and reach the two antibody immobilized regions at the same time. That is, the two substances to be analyzed can be measured under the same condition, so that improvement in measurement quantitativeness can be expected.

EXAMPLE 8

Figure 12:
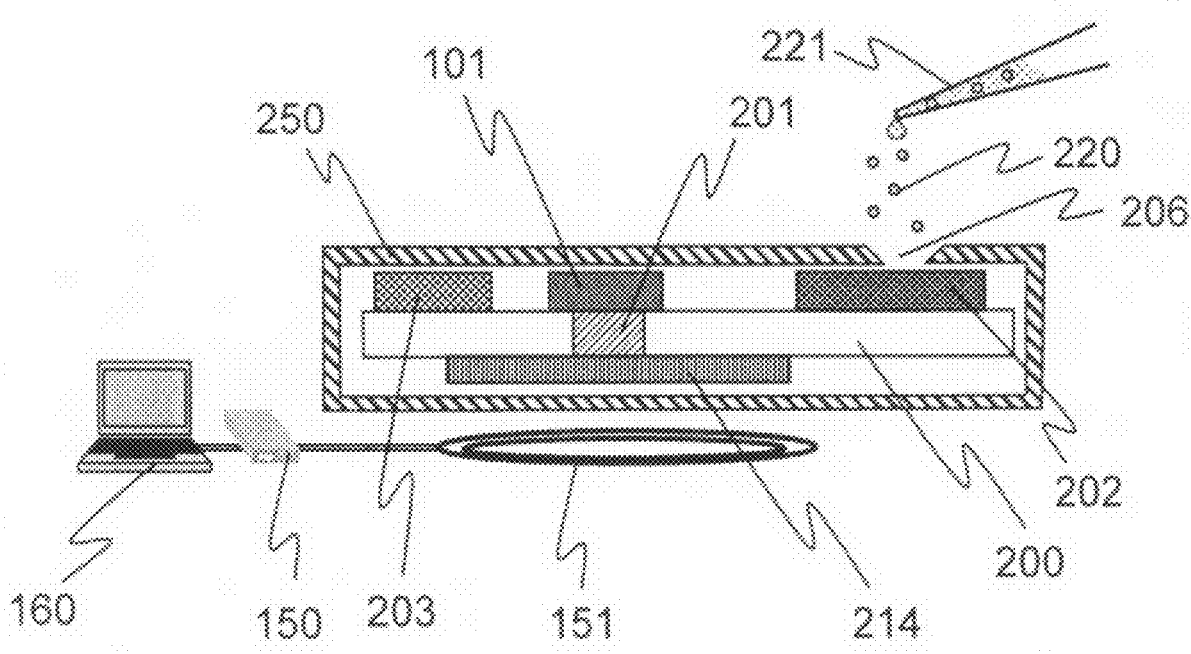
FIG. 12 explains an example of a method for improving sensitivity by using a mirror.

As an eighth example, a description will be made of the case where a reflective mirror is used with reference to FIG. 12. Chemical luminescence generated through a chemical luminescence reaction in the antibody immobilized section 201 is irregularly reflected in the membrane 200. A light reflective mirror is therefore disposed on the opposite side to the side where the sensor element 101 is disposed. In this way, part of the light that is directed to the opposite side to the sensor element and hence cannot be used as the signal can be acquired into the light receiving section of the sensor element, allowing improvement in sensitivity.

EXAMPLE 9

Figure 13:
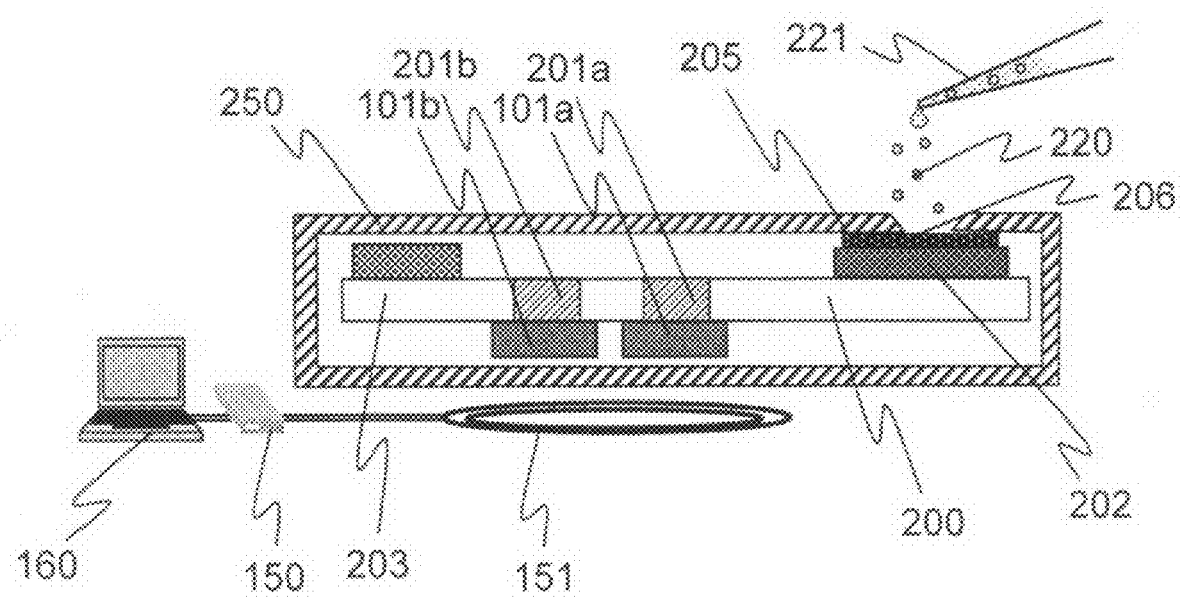
FIG. 13 explains an example of the arrangement of sensor elements.

As a ninth example, a description will be made of the case where the sensor element is disposed under the membrane with reference to FIG. 13.

In the shielding container 250, the sample introduction section 206 is typically provided on the upper side against the gravity from the viewpoint of workability. The reader coil is disposed on the lower side along the gravity, that is, on the opposite side to the sample introduction section 206 from the viewpoint of workability. The sensor elements 101a and 101b are then disposed on the opposite side of the membrane 200 to the sample introduction section 206. In this way, the sensor elements can be disposed closer to the reader coil by the thickness of the membrane 200, allowing an increased size of the gap between the shielding container 250 and the reader coil 151. Accordingly, when the shielding container 250 is placed close to the reader coil 151, the degree of freedom of distance between the reader coil and the sensor elements increases, allowing a stable communication to be achieved.

EXAMPLE 10

Figure 14:
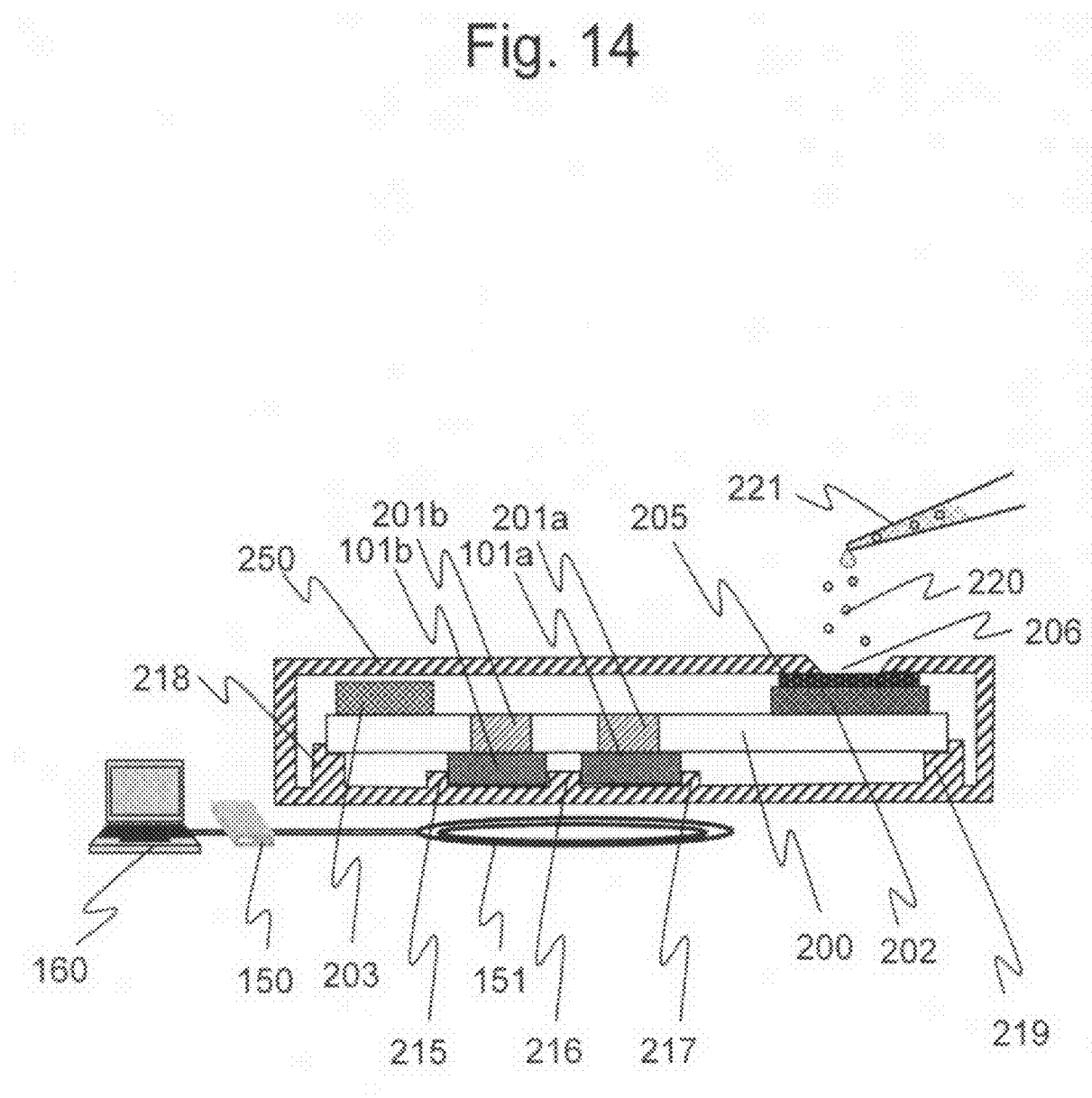
FIG. 14 explains an example of a guide structure for positioning the sensor element.

As a tenth example, a description will be made of the case where a guide is disposed in the shielding container with reference to FIG. 14.

In this example, structures 215, 216 and 217 are provided, each serving as a guide when sensor elements are disposed in the shielding container. The sensor elements 101a and 101b can thus be easily and accurately positioned when the reaction analysis kit is fabricated. Furthermore, by providing positioning guides 218 and 219 for the membrane 200, the positional relationship between the membrane 200 and the sensor elements 101a and 101b can be easily and accurately determined.

EXAMPLE 11

As an eleventh example, a description will be made of an example of detection when chemical luminescence is generated according to Example 1 with reference to FIGS. 15 to 18.

FIG. 15 shows a chemical luminescence image acquired with a CCD. As a sample, hCG having a concentration of 1 μg/ml was used. Although chemical luminescence is observed along the antibody immobilized region 201, it is revealed that the luminescence intensity distribution along the line A-A' shown in FIG. 15(b) varies depending on the position on the line A-A' as shown in FIG. 15(c). This intensity variation is attributable to the variation in the density of the immobilized antibody. When a dispenser is used to immobilize the antibody, the antibody immobilized region is formed by setting the discharge speed of the antibody solution to a fixed value and moving the discharge nozzle at a fixed speed. It is however difficult to keep the discharge speed constant because of the effect of the surface tension at the tip of the discharge nozzle. Therefore, the amount of discharge is set to a fixed value, and then the antibody is immobilized at one location. In this way, the discharge speed is not necessarily constant. After checking that a predetermined amount is discharged at a predetermined position, the nozzle can be moved to the next position where the antibody is immobilized. If the surface tension causes variation in the amount of the solution separated from the nozzle, by setting in advance a certain amount of discharge at which a stable separation is achieved, a fixed amount can be immobilized to one location.

Since a coloring reaction is visually checked in conventional chromatography, a linear antibody immobilized pattern has been frequently used from the viewpoint of visibility. However, since the sensor element is used to detect luminescence in the present invention, a fixed amount of antibody may be distributed across a limited luminescence detection area as shown in FIG. 16. When the antibody solution is discharged at a fixed position, it is desirable to optimize the relationship between the light receiving section of the sensor element and the antibody immobilized section. That is, the antibody is uniformly distributed across the size a of the light receiving section as shown in FIG. 17(a), or the whole antibody is distributed within the region a as shown in FIG. 17(b). Accordingly, by thus configuring the portion having a large change on the antibody distribution curve not to overlap with the light receiving section, it is possible to reduce variation in characteristics of the reaction analysis kit due to the shift in position of the sensor element when the reaction analysis kit is assembled.

When a dispenser is used to immobilize the antibody in the membrane, the concentration distribution of the antibody is shaped in such a way that there are tails at the peripheral of the distribution curve as shown in the hatched portions in FIGS. 17(c) and 17(d). Such tail regions cause crosstalk to the sensor element above an adjacent antibody when different antibodies are arranged side by side, as described later with reference to FIG. 18(b), or cause a trouble when a plurality of antibodies are arranged at a high density. Such a problem can be solved by inactivating the antibody in the tail regions. To inactivate the antibody, the following measures can be used: (i) applying light to the antibody with a mask fabricated by machining a metal plate covering the tail regions (hatched portions shown in FIGS. 17(c) and 17(d)), (ii) bringing a hot metal die (heated to a temperature of 100° C. or higher, for example) having the same shape as the tail regions in contact with the tail regions, and (iii) submerging the antibody in a solution having a pH that modifies the antibody with the region other than the tail regions covered.

By thus shaping the antibody immobilized region into a spot (substantially circular), when a plurality of substances to be analyzed are handled, antibody immobilized sections 205a and 205b can be disposed in the direction perpendicular to the direction in which the sample solution flows as shown in FIG. 18(b). If the antibody immobilized pattern is linear, lines must be sequentially arranged in the direction in which the sample solution flows as shown in FIG. 18(a). In such an arrangement, since substances to be analyzed corresponding to 201a and 201b flow through different distances in the membrane, it is difficult to perform comparative quantification. According to the antibody immobilized pattern shown in FIG. 18(b), the substances to be analyzed corresponding to 205a and 205b are measured under the same condition, allowing comparative quantification to be performed. In FIG. 18(b), the size b of the sensor element limits the size a and the layout distance d of the antibody immobilized pattern as follows: (i) a<b from the viewpoint of reduction in crosstalk, and (ii) d>b from the physical limitation required for the sensor elements not to overlap each other. When the sensor elements 101a and 101b are disposed at an interval of d' so that they do not overlap each other, (iii) d=d'.

EXAMPLE 12

As a twelfth example, a description will be made of the case where a light absorbing region is provided with reference to FIG. 19. When a plurality of substances to be analyzed are handled, provision of a light absorbing region 213 or 214 between the antibody immobilized regions as shown in FIG. 19 allows reduction in crosstalk. To form the light absorbing region, the same method as used in Example 2 can be used.

EXAMPLE 13

As a thirteenth example, a description will be made of the case where a sensor element-side coil is used with reference to FIG. 20.

First, a sensor element-side coil 254 is disposed in the shielding container and connected to the sensor element 101. The sensor element-side coil 254 and the sensor element 101 are configured such that pads 255 of the sensor element-side coil face pads 110 of the sensor element, and connecting means 111, such as flip-chip, wire bonding and a conductive adhesive, is used to connect the sensor element 101 to the sensor element-side coil 254. In this process, use of an anisotropic conductive film as the connecting means allows connection in a simpler process.

In this way, use of the sensor element-side coil allows the diameter of the coil to be determined without limitation imposed by the size of the sensor element. The communication distance between the reaction analysis kit and the reader can therefore increase, allowing improvement in convenience at analysis sites.

EXAMPLE 14

As a fourteenth example, a description will be made of the case where a relay coil is disposed in the shielding container with reference to FIG. 21.

In this example, a communication coil is formed on the sensor element 101. A relay coil 256 consists of a portion that faces the sensor element-side coil, a portion that faces the reader coil, and a matching circuit. Use of such a relay coil allows the diameter of the coil to be determined without limitation imposed by the size of the sensor element. The communication distance between the reaction analysis kit and the reader can therefore increase, allowing improvement in convenience at analysis sites.

The present invention provides a simple, inexpensive reaction analysis kit and analysis apparatus capable of performing highly sensitive, quantitative measurement using an immunochromatography technique. The analysis apparatus according to the present invention is provided as a compact, disposable kit. The analysis apparatus is therefore useful as a POCT (Point of Care Testing) device for disease markers, viruses and bacteria in diagnosis, prevention and treatment of lifestyle-related diseases, such as cancers, infectious diseases and cardiac infarction.

What is claimed is:

1. A reaction analysis system comprising:

a reaction detection plate including a) a membrane, b) a first antibody impregnated section that is disposed such that it faces the membrane and holds a first labeled antibody that specifically binds to a substance to be analyzed, c) a second antibody immobilized section that is disposed in part of the membrane and has an immobilized second antibody, the second antibody specifically binding to the substance to be analyzed, d) a sensor element that is disposed such that it faces the second antibody immobilized section and includes a light detector and a signal transceiver, the sensor element being disposed in close contact with the second antibody immobilized section, and e) an absorbing section disposed such that the absorbing section faces the membrane and absorbs the sample, wherein the sensor element detects a chemical luminescence generated by a reaction between a labeling substance of the first labeled antibody and a reagent that reacts with the labeling substance and emits light;

a shielding container that houses the reaction detection plate, the shielding container having a sample introduction section for introducing a sample into the reaction detection plate, wherein the second antibody immobilized section is disposed between the sample introduction section and the absorbing section;

a reader coil that is disposed outside the shielding container, the reader coil transmitting and receiving a signal to and from the sensor element and supplying power to the sensor element;

a reader that performs demodulation/modulation, decoding/coding and amplification of the signal; and a processor for executing an application program that controls the sensor element.

2. The reaction analysis system according to claim 1 further comprising a sensor element-side coil in the shielding container.

3. The reaction analysis system according to claim 2 further comprising a relay coil that inductively couples the sensor element-side coil to the reader coil.

4. The reaction analysis system according to claim 1, wherein the number of the sensor element is at least two.

* * * * *